United States Patent
Old

(10) Patent No.: US 7,795,287 B2
(45) Date of Patent: Sep. 14, 2010

(54) THERAPEUTIC SUBSTITUTED HYDANTOINS AND RELATED COMPOUNDS

(75) Inventor: David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 38 days.

(21) Appl. No.: 11/847,779

(22) Filed: Aug. 30, 2007

(65) Prior Publication Data

US 2008/0058397 A1    Mar. 6, 2008

Related U.S. Application Data

(60) Provisional application No. 60/824,310, filed on Sep. 1, 2006.

(51) Int. Cl.
*A61K 31/426* (2006.01)
*A61K 31/4166* (2006.01)
*A61K 31/4178* (2006.01)
*A61P 27/02* (2006.01)
*C07D 277/20* (2006.01)
*C07D 233/02* (2006.01)

(52) U.S. Cl. ............... 514/369; 514/374; 514/385; 514/391; 514/444; 548/315.1; 548/319.5; 548/254; 548/221; 548/235; 548/185; 549/59; 549/505

(58) Field of Classification Search ............ 514/315.1, 514/444, 385, 391, 374, 369; 548/315.1, 548/319.5; 549/59
See application file for complete search history.

(56) References Cited

U.S. PATENT DOCUMENTS 5,902,726 A    5/1999   Kliewer et al.

2006/0148894 A1   7/2006   Donde et al.
2009/0062361 A1*   3/2009   Old ..................... 514/391

FOREIGN PATENT DOCUMENTS

EP    0253 094 A    1/1988

OTHER PUBLICATIONS

Wu and Farrelly, Toxicology 236:1-6, 2007.*
Journal of Medicinal Chemistry (1973), 16(11), p. 1308-10 by Islip et al.*
Dragoli, et al., "Parallel Synthesis of Prostaglandin $E_1$ Analogues," J. Comb. Chem., 1999, 1, pp. 534-539.
Baxter, et al., "Synthesis and Use of 7-Substituted Norbornadienes + for the Preparation of Prostaglandins and Prostanoids," J. Chem. SOc. Perkin Trans., I, 1986, pp. 889-900.

* cited by examiner

*Primary Examiner*—Yong Chu
(74) *Attorney, Agent, or Firm*—Kevin J. Forrestal; John E. Wurst; Doina G. Ene

(57) ABSTRACT

A compound having a structure

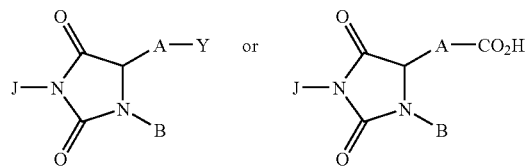

is disclosed herein. Therapeutic methods, compositions, and medicaments related thereto are also disclosed.

11 Claims, No Drawings

THERAPEUTIC SUBSTITUTED HYDANTOINS AND RELATED COMPOUNDS

RELATED APPLICATION

This application claims the benefit of U.S. Provisional Application Ser. No. 60/824,310, filed Sep. 1, 2006, which is hereby incorporated by reference in its entirety.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

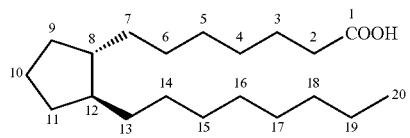

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Disclosed herein is a compound having a structure

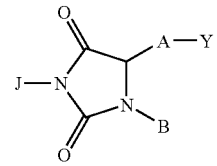

or a pharmaceutically acceptable salt thereof, or a prodrug thereof;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —$CH$=$CH$— or —$C$≡$C$—;

J is H, $R^1$, $C(O)R^1$, or $SO_2R^1$; wherein $R^1$ is $C_{1-6}$ alkyl, phenyl, or biphenyl; and B is aryl or heteroaryl.

Also disclosed herein is a carboxylic acid or a bioisostere thereof, said carboxylic acid having a structure

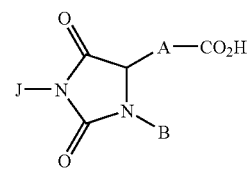

or a pharmaceutically acceptable salt thereof, or a prodrug thereof;

wherein A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —$CH$=$CH$— or —$C$≡$C$—;

J is H, $R^1$, $C(O)R^1$, or $SO_2R^1$; wherein $R^1$ is $C_{1-6}$ alkyl, phenyl, or biphenyl; and B is aryl or heteroaryl.

In one embodiment, if B is unsubstituted aryl or heteroaryl and $J^1$ is H, $J^2$ is not H.

"Bioisosteres are substituents or groups that have chemical or physical similarities, and which produce broadly similar biological properties." Silverman, Richard B., *The Organic Chemistry of Drug Design and Drug Action*, 2$^{nd}$ Edition, Amsterdam: Elsevier Academic Press, 2004, p. 29.

While not intending to be limiting, organic acid functional groups are bioisosteres of carboxylic acids. An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Additionally, an amide or ester of one of the organic acids mentioned above comprising up to 14 carbon atoms is also contemplated. In an ester, a hydrocarbyl moiety replaces a hydrogen atom of an acid such as in a carboxylic acid ester, e.g. $CO_2Me$, $CO_2Et$, etc.

In an amide, an amine group replaces an OH of the acid. Examples of amides include $CON(R^2)_2$, $CON(OR^2)R^2$, $CON(CH_2CH_2OH)_2$, and $CONH(CH_2CH_2OH)$ where $R^2$ is independently H, $C_1$-$C_6$ alkyl, phenyl, or biphenyl. Moieties such as $CONHSO_2R^2$ are also amides of the carboxylic acid notwithstanding the fact that they may also be considered to be amides of the sulfonic acid $R^2$—$SO_3H$. The following amides are also specifically contemplated, $CONSO_2$-biphenyl, $CONSO_2$-phenyl, $CONSO_2$-heteroaryl, and $CONSO_2$-naphthyl. The biphenyl, phenyl, heteroaryl, or naphthyl may be substituted or unsubstituted.

Han et. al. (Biorganic & Medicinal Chemistry Letters 15 (2005) 3487-3490) has recently shown that the groups shown below are suitable bioisosteres for a carboxylic acid. The activity of compounds with these groups in inhibiting HCV NS3 protease was comparable to or superior to similar compounds where the group is replaced by $CO_2H$. Thus, Y could be any group depicted below.

Carboxylic Acid Bioisosteres According to Han et. al.

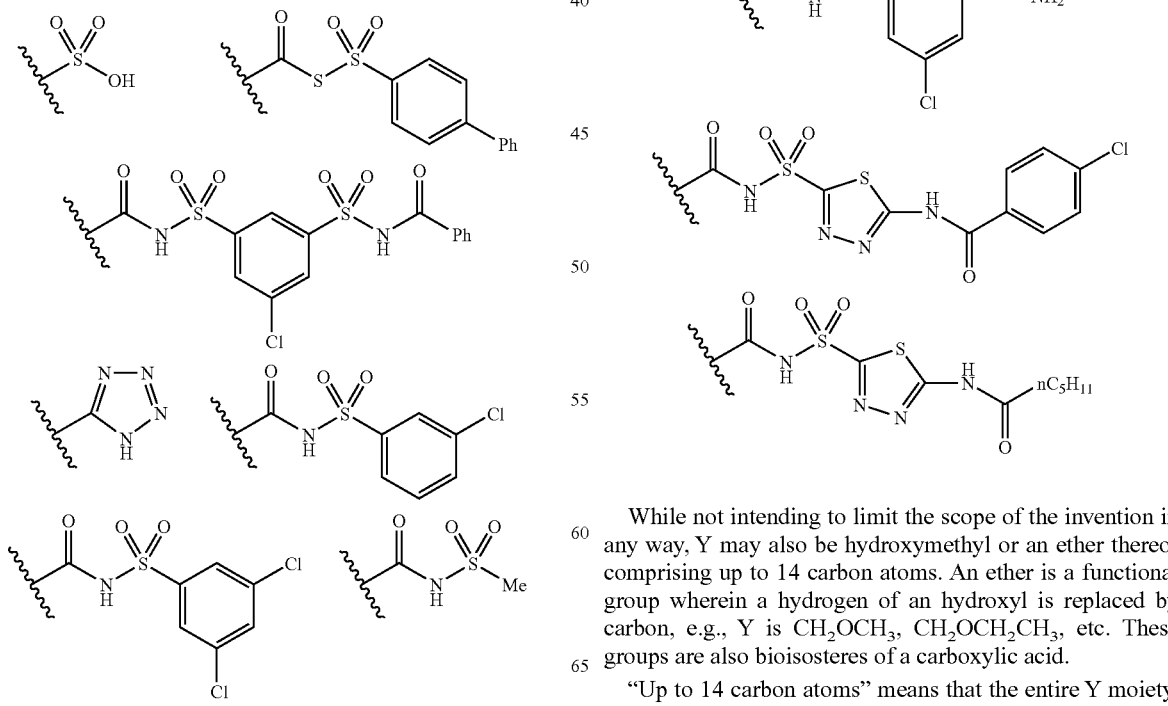

While not intending to limit the scope of the invention in any way, Y may also be hydroxymethyl or an ether thereof comprising up to 14 carbon atoms. An ether is a functional group wherein a hydrogen of an hydroxyl is replaced by carbon, e.g., Y is $CH_2OCH_3$, $CH_2OCH_2CH_3$, etc. These groups are also bioisosteres of a carboxylic acid.

"Up to 14 carbon atoms" means that the entire Y moiety, including the carbonyl carbon of a carboxylic acid ester or amide, and both carbon atoms in the —CH$_2$O—C of an ether has 0, 1, 2, 3, 4, 5, 6, 7, 8, 9, 10, 11, 12, 13, or 14 carbon atoms.

Finally, while not intending to limit the scope of the invention in any way, Y may be a tetrazolyl functional group.

While not intending to be limiting, examples of compounds having the identified Y are depicted below. In these examples R is H or hydrocarbyl, subject to the constraints defined herein. Each structure below represents a specific embodiment which is individually contemplated, as well as pharmaceutically acceptable salts and prodrugs of compounds which are represented by the structures. However, other examples are possible which may not fall within the scope of the structures shown below.

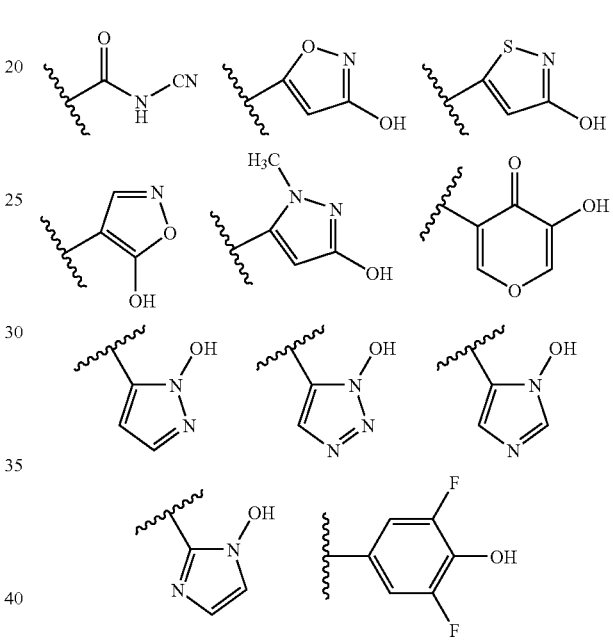

A tetrazolyl functional group is another bioisostere of a carboxylic acid. An unsubstituted tetrazolyl functional group has two tautomeric forms, which can rapidly interconvert in aqueous or biological media, and are thus equivalent to one another. These tautomers are shown below.

Additionally, if R$^2$ is C$_1$-C$_6$ alkyl, phenyl, or biphenyl, other isomeric forms of the tetrazolyl functional group such as the one shown below are also possible, unsubstituted and hydrocarbyl substituted tetrazolyl up to C$_{12}$ are considered to be within the scope of the term "tetrazolyl."

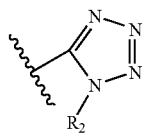

While not intending to limit the scope of the invention in any way, in one embodiment, Y is CO$_2$R$^2$, CON(R$^2$)$_2$, CON(OR$^2$)R$^2$, CON(CH$_2$CH$_2$OH)$_2$, CONH(CH$_2$CH$_2$OH), CH$_2$OH, P(O)(OH)$_2$, CONHSO$_2$R$^2$, SO$_2$N(R$^2$)$_2$, SO$_2$NHR$^2$,

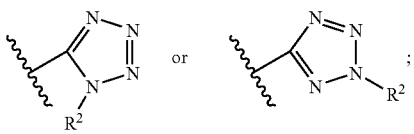

wherein R$^2$ is independently H, C$_1$-C$_6$ alkyl, unsubstituted phenyl, or unsubstituted biphenyl.

According to Silverman (p. 30), the moieties shown below are also bioisosteres of a carboxylic acid.

Carboxylic Acid Bioisosteres According to Silverman

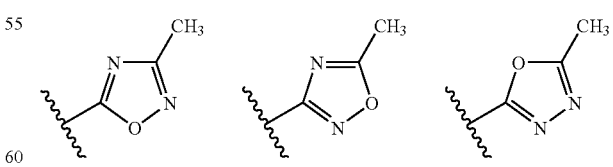

Orlek et al. (*J. Med. Chem.* 1991, 34, 2726-2735) described oxadiazoles as suitable bioisosteres for a carboxylic acid. These ester replacements were shown to be potent muscarinic agonists having improved metabolic stability. Oxadiazoles were also described by Anderson et al. (Eur. J. Med. Chem. 1996, 31, 417-425) as carboxamide replacements having improved in vivo efficacy at the benzodiazepine receptor.

Carboxylic Acid Bioisosteres According to Orlek et. al.

Kohara et al. (*J. Med. Chem.* 1996, 39, 5228-5235) described acidic heterocycles as suitable bioisosteres for a tetrazole. These carboxylic acid replacements were shown to be potent angiotensin II receptor antagonists having improved metabolic stability.

Tetrazole Bioisosteres According to Kohara et. al.

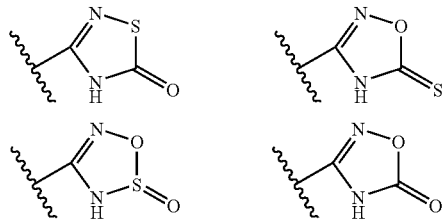

Drysdale et al. (*J. Med. Chem.* 1992, 35, 2573-2581) have described carboxylic acid mimics of non-peptide CCK-B receptor antagonists. The binding affinities of many of the bioisosteres are similar to the parent carboxylic acid.

Carboxylic Acid Bioisosteres According to Drysdale et. al.

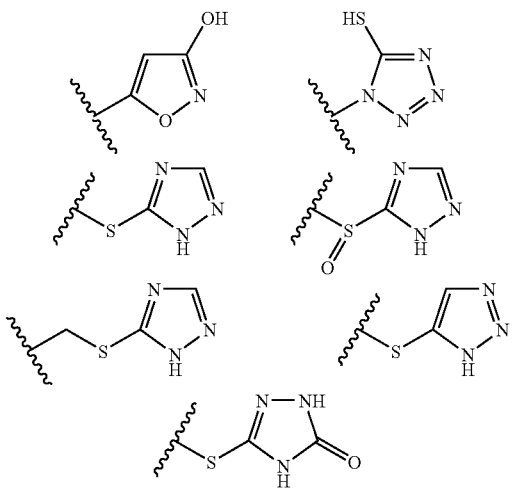

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$— may be replaced by —CH=CH— or —C≡C—.

Thus, A may be —(CH$_2$)$_6$—, cis —CH$_2$CH=CH—(CH$_2$)$_3$—, or —CH$_2$C≡C—(CH$_2$)$_3$—.

Alternatively, A may be a group which is related to one of these three moieties in that any carbon is replaced with S or O. For example, A may be a moiety where S replaces one or two carbon atoms such as one of the following or the like.

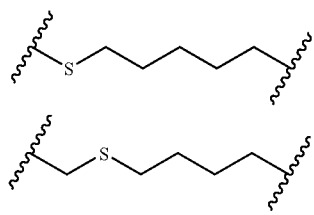

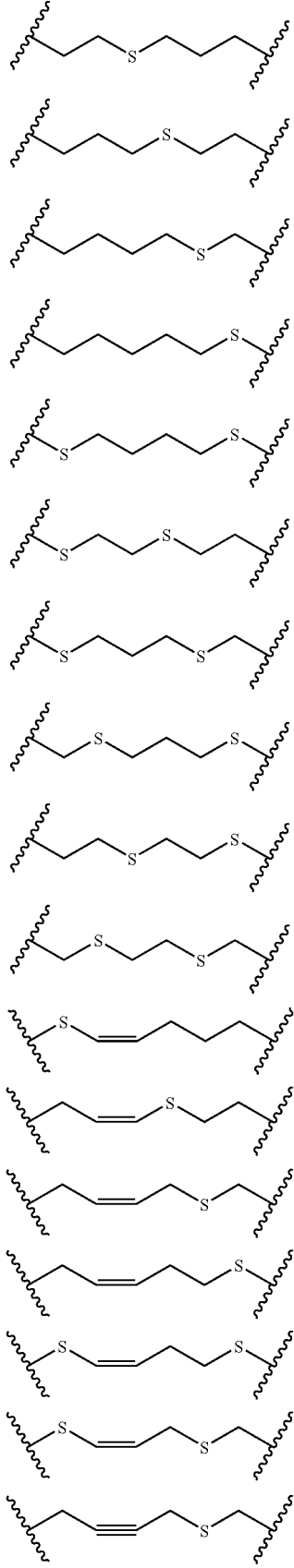

-continued

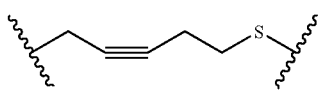

Alternatively, A may be a moiety where O replaces one or two carbon atoms such as one of the following or the like.

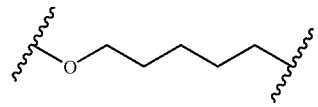
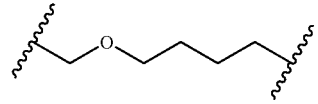
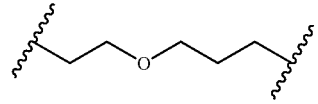
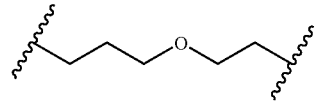
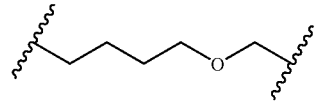
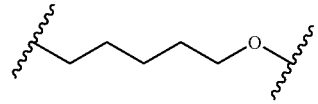
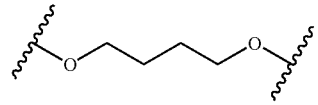
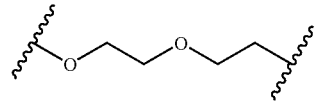
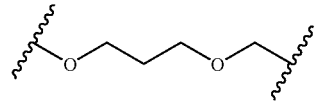
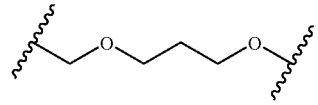
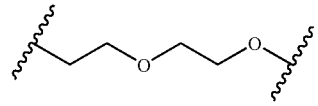
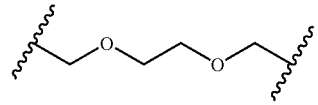
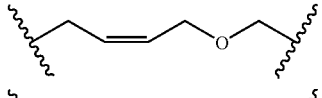
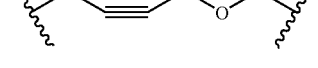

Alternatively, A may have an O replacing one carbon atom and an S replacing another carbon atom, such as one of the following or the like.

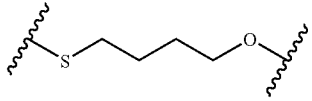
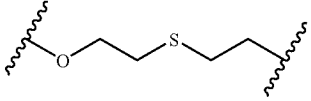
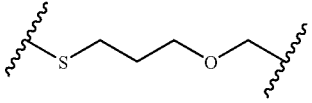
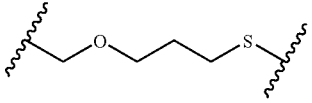
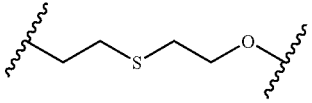

Alternatively, in certain embodiments A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—. In other words, in one embodiment A comprises:
  1) a) 1, 2, 3, or 4 —$CH_2$— moieties, or
     b) 0, 1 or 2 —$CH_2$— moieties and —CH=CH— or —C≡C—; and
  2) Ar;
e.g. —$CH_2$—Ar—, —$(CH_2)_2$—Ar—, —CH=CH—Ar—, —C≡C—Ar—, —$CH_2$—Ar—$CH_2$—, —$CH_2$Ar—$(CH_2)_2$—, —$CH_2$Ar—CH=CH—, —$CH_2$Ar—C≡C—, —$(CH_2)_2$—Ar—$(CH_2)_2$—, and the like;

in another embodiment A comprises:
  1) a) O; and 0, 1, 2, or 3 —$CH_2$— moieties; or
     b) O; and 0 or 1 —$CH_2$— moieties and —CH=CH— and —C≡C—; and
  2) Ar;
e.g., —O—Ar—, —Ar—$CH_2$—O—, —O—Ar—$(CH_2)_2$—, —OAr—CH=CH—, —O—Ar—C≡C—, —O—$CH_2$—Ar—, —O—$CH_2$—Ar—$(CH_2)_2$, —O—$CH_2$Ar—CH=CH—, —O—$CH_2$Ar—C≡C—, and the like; or in another embodiment A comprises:
  1) a) S; and 0, 1, 2, or 3 —$CH_2$— moieties; or
     b) S; and 0 or 1 —$CH_2$— moieties and —CH=CH— or —C≡C—; and
  2) Ar;
e.g., —S—Ar—, —Ar—$CH_2$—S—, —S—Ar—$(CH_2)_2$—, —SAr—CH=CH—, —S—Ar—C≡C—, —S—$CH_2$—Ar—, —S—$CH_2$—Ar—$(CH_2)_2$, —S—$CH_2$Ar—CH=CH—, —S—$CH_2$Ar—C≡C—, and the like.

In another embodiment, the sum of m and o is 2, 3, or 4 wherein one $CH_2$ may be replaced with S or O and 1 —$CH_2$—$CH_2$— may be replaced by —CH=CH— or —C≡C—.

In another embodiment, the sum of m and o is 3 wherein one $CH_2$ may be replaced with S or O and 1 —$CH_2$—$CH_2$— may be replaced by —CH=CH— or —C≡C—.

In another embodiment, the sum of m and o is 2 wherein one $CH_2$ may be replaced with S or O or 1 —$CH_2$—$CH_2$— may be replaced by —CH=CH— or —C≡C—.

In another embodiment, the sum of m and o is 4 wherein one $CH_2$ may be replaced with S or O and 1 —$CH_2$—$CH_2$— may be replaced by —CH=CH— or —C≡C—.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —$(CH_2)_2$-Ph-. Substituents of Ar each have from 0 to 4 carbon atoms, from 0 to 3 oxygen atoms, from 0 to 2 sulfur atoms, from 0 to 2 nitrogen atoms, from 0 to 3 fluorine atoms, from 0 to 1 chlorine atoms, from 0 to 1 bromine atoms, from 0 to 1 iodine atoms, and from 0 to 10 hydrogen atoms.

In another embodiment A is —$CH_2$—Ar—$OCH_2$—. In another embodiment A is —$CH_2$-Ph-$OCH_2$—. In another embodiment, Ph is attached at the 1 and 3 positions, otherwise known as m-interphenylene, such as when A has the structure shown below.

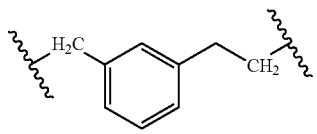

In another embodiment A is —$(CH_2)_6$—, cis —$CH_2CH=CH$—$(CH_2)_3$—, or —$CH_2C≡C$—$(CH_2)_3$—, wherein 1 or 2 carbon atoms may be replaced with S or O; or A is —$(CH_2)_2$-Ph- wherein one —$CH_2$— may be replaced with S or O.

In another embodiment A is —$(CH_2)_6$—, cis —$CH_2CH=CH$—$(CH_2)_3$—, or —$CH_2C≡C$—$(CH_2)_3$—, wherein 1 or 2 carbon atoms may be replaced with S or O; or A is —$(CH_2)_2$-Ph-.

In one embodiment, Ar is thienyl.

In other embodiments, A has one of the following structures.

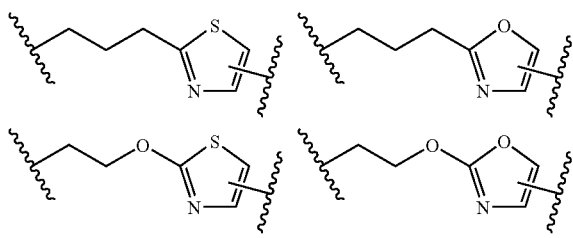

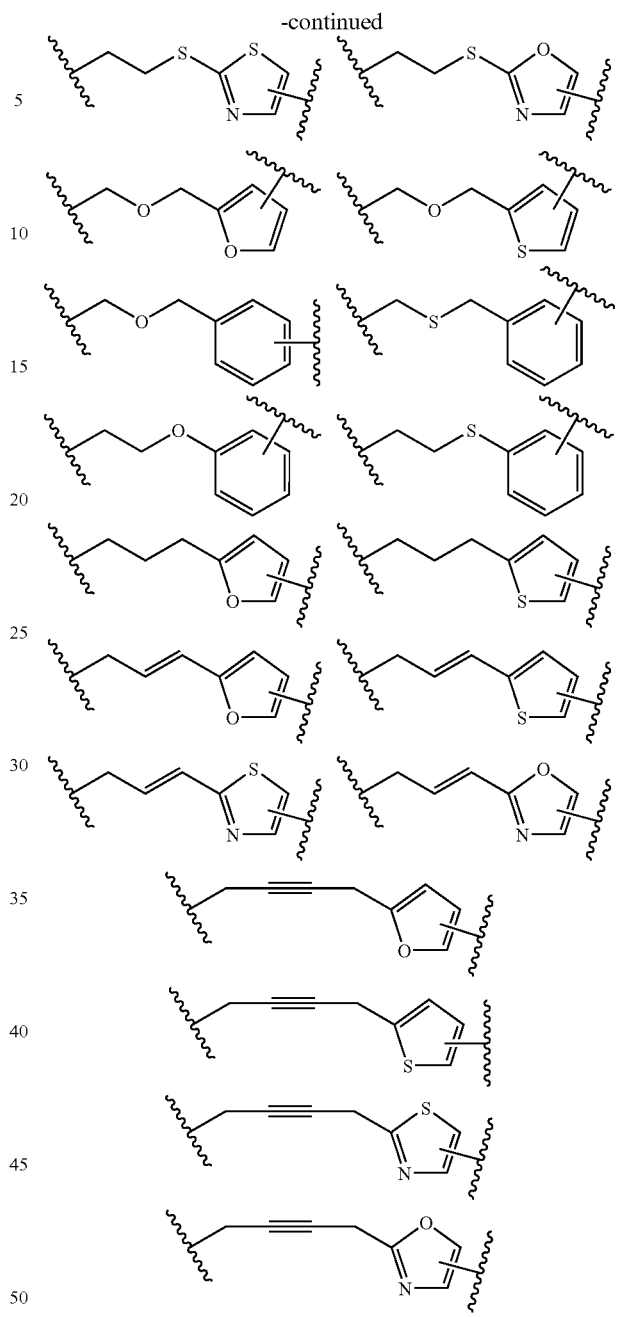

In another embodiment A is —$CH_2OCH_2Ar$—.
In another embodiment A is —$CH_2SCH_2Ar$—.
In another embodiment A is —$(CH_2)_3Ar$—.
In another embodiment A is —$CH_2O(CH_2)_4$—.
In another embodiment A is —$CH_2S(CH_2)_4$—.
In another embodiment A is —$(CH_2)_6$—.
In another embodiment A is cis —$CH_2CH=CH$—$(CH_2)_3$—.
In another embodiment A is —$CH_2C≡C$—$(CH_2)_3$—.
In another embodiment A is —$S(CH_2)_3S(CH_2)_2$—.
In another embodiment A is —$(CH_2)_4OCH_2$—.
In another embodiment A is cis —$CH_2CH=CH$—$CH_2OCH_2$—.
In another embodiment A is —$CH_2CH=CH$—$CH_2OCH_2$—.

In another embodiment A is —(CH$_2$)$_2$S(CH$_2$)$_3$—.
In another embodiment A is —CH$_2$-Ph-OCH$_2$—, wherein Ph is interphenylene.
In another embodiment A is —CH$_2$-mPh-OCH$_2$—, wherein mPh is m-interphenylene.
In another embodiment A is —CH$_2$—O—(CH$_2$)$_4$—.
In another embodiment A is —CH$_2$—O—CH$_2$—Ar—, wherein Ar is 2,5-interthienylene.
In another embodiment A is —CH$_2$—O—CH$_2$—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-(methoxymethyl)phenyl.
In another embodiment A is 3-(3-propylphenyl).
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. A substituent must be stable enough for the compound to be useful as described herein. In addition to the atoms listed above, a substituent may also have a metal cation or any other stable cation having an atom not listed above if the substituent is acidic and the salt form is stable. For example, —OH may form an —O.Na$^+$ salt or CO$_2$H may form a CO$_2$.K$^+$ salt. Any cation of the salt is not counted in the "4 or less heavy atoms." Thus, the substituent may be hydrocarbyl having up to 4 carbon atoms, including alkyl up to C$_4$, alkenyl, alkynyl, and the like;
hydrocarbyloxy up to C$_3$;
organic acid such as CO$_2$H, SO$_3$H, P(O)(OH)$_2$, and the like, and salts thereof;
CF$_3$;
halo, such as F, Cl, or Br;
hydroxyl;
NH$_2$ and alkylamine functional groups up to C$_3$;
other N or S containing substituents such as CN, NO$_2$, and the like;
and the like.

In one embodiment A is —(CH$_2$)$_m$-Ph-(CH$_2$)$_o$— wherein the sum of m and o is 1, 2, or 3, and wherein one CH$_2$ may be replaced with S or O.

In another embodiment A is —CH$_2$—Ar—OCH$_2$—. In another embodiment A is —CH$_2$-Ph-OCH$_2$—. In another embodiment, Ph is attached at the 1 and 3 positions, otherwise known as m-interphenylene, such as when A has the structure shown below.

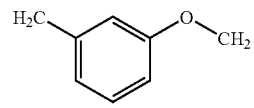

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one CH$_2$ may be replaced with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In other embodiments, A has one of the following structures, where Y is attached to the aromatic or heteroaromatic ring.

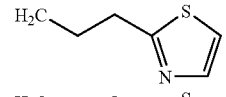 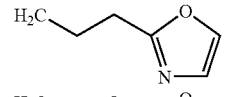
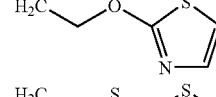 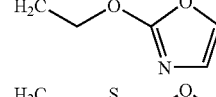
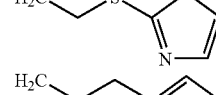 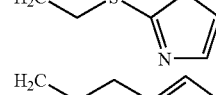
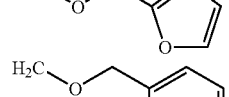 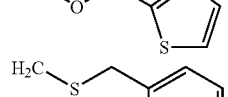
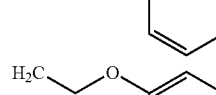 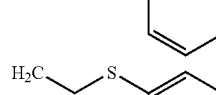
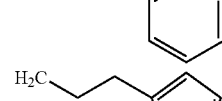 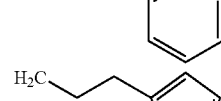
 

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$O(CH$_2$)$_4$.
In another embodiment A is —CH$_2$S(CH$_2$)$_4$.
In another embodiment A is —(CH$_2$)$_6$—.
In another embodiment A is cis —CH$_2$CH=CH—(CH$_2$)$_3$—.
In another embodiment A is —CH$_2$C≡C—(CH$_2$)$_3$—.
In another embodiment A is —S(CH$_2$)$_3$S(CH$_2$)$_2$—.
In another embodiment A is —(CH$_2$)$_4$OCH$_2$—.

In another embodiment A is cis —CH₂CH═CH—CH₂OCH₂—.

In another embodiment A is —CH₂CH≡CH—CH₂OCH₂—.

In another embodiment A is —(CH₂)₂S(CH₂)₃—.

In another embodiment A is —CH₂-Ph-OCH₂—, wherein Ph is interphenylene.

In another embodiment A is —CH₂-mPh-OCH₂—, wherein mPh is m-interphenylene.

In another embodiment A is —CH₂—O—(CH₂)₄—.

In another embodiment A is —CH₂—O—CH₂—Ar—, wherein Ar is 2,5-interthienylene.

In another embodiment A is —CH₂—O—CH₂—Ar—, wherein Ar is 2,5-interfurylene.

In another embodiment A is (3-methylphenoxy)methyl.

In another embodiment A is (4-but-2-ynyloxy)methyl.

In another embodiment A is 2-(2-ethylthio)thiazol-4-yl.

In another embodiment A is 2-(3-propyl)thiazol-5-yl.

In another embodiment A is 3-methoxymethyl)phenyl.

In another embodiment A is 3-(3-propylphenyl.

In another embodiment A is 3-methylphenethyl.

In another embodiment A is 4-(2-ethyl)phenyl.

In another embodiment A is 4-phenethyl.

In another embodiment A is 4-methoxybutyl.

In another embodiment A is 5-(methoxymethyl)furan-2-yl.

In another embodiment A is 5-(methoxymethyl)thiophen-2-yl.

In another embodiment A is 5-(3-propyl)furan-2-yl.

In another embodiment A is 5-(3-propyl)thiophen-2-yl.

In another embodiment A is 6-hexyl.

In another embodiment A is (Z)-6-hex-4-enyl.

Compounds according to the each of the structures depicted below, and pharmaceutically acceptable salts thereof, and prodrugs thereof, are contemplated as individual embodiments. In other words, each structure represents a different embodiment.

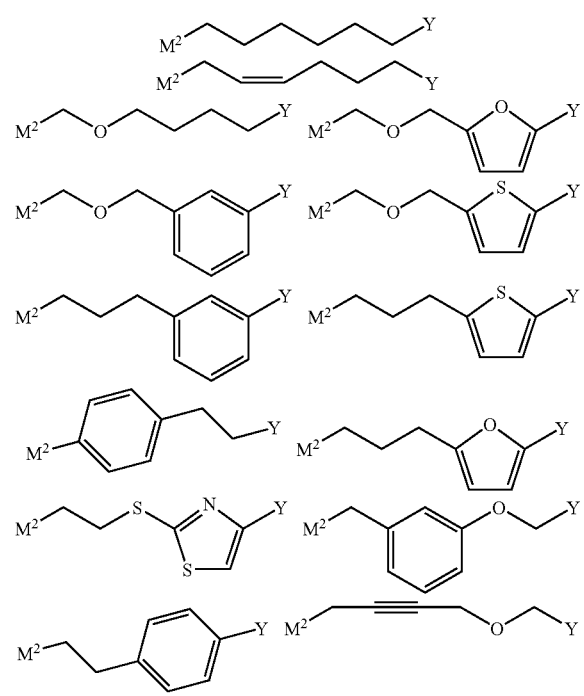

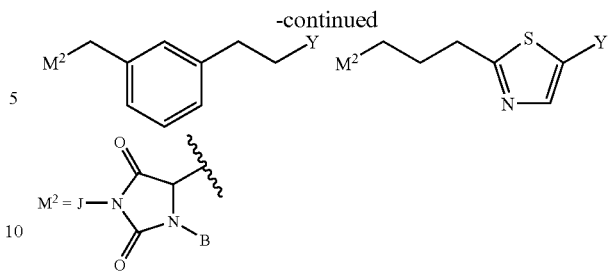

J is H, R¹, C(O)R¹, or SO₂R¹; wherein R¹ is $C_{1-6}$ alkyl, phenyl, or biphenyl. In one embodiment R¹ is $C_{1-3}$ alkyl, i.e. alkyl having 1, 2, or 3 carbon atoms.

In another embodiment, R¹ is phenyl.

In another embodiment, R¹ is biphenyl.

In one embodiment J is H.

In another embodiment J is SO₂CH₃.

In another embodiment J is CO₂CH₃.

In another embodiment J is $C_{1-6}$ alkyl.

Thus, each of the structures below is contemplated. These structures, or pharmaceutically acceptable salts thereof, or prodrugs thereof, individually represent a compound which is an embodiment contemplated herein. In other words, each structure represents a different embodiment.

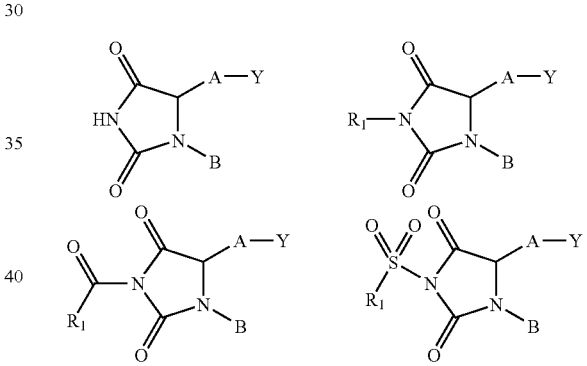

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

Aryl or heteroaryl may be substituted or unsubstituted. A substituent of aryl or heteroaryl may have up to 20 non-hydrogen atoms each in any stable combination and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. A substituent must be sufficiently stable for the compound, salt, or prodrug to be useful as described herein. In addition to the atoms listed above, a substituent may also have a metal cation or other stable cation having an atom not listed above if the substituent is acidic and the salt form is stable. For example, —OH may form an —O.Na⁺ salt or CO₂H may form a CO₂.K⁺ salt. Thus, while not intending to limit the scope of the invention in any way, a substituent may be:

hydrocarbyl, i.e. a moiety consisting of only carbon and hydrogen such as alkyl, alkenyl, alkynyl, and the like, including linear, branched or cyclic hydrocarbyl, and combinations thereof;

Alkyl is hydrocarbyl having no double or triple bonds;

$C_{1-6}$ alkyl is alkyl having 1, 2, 3, 4, 5, or 6 carbon atoms;

hydrocarbyloxy, meaning O-hydrocarbyl such as $OCH_3$, $OCH_2CH_3$, O-cyclohexyl, etc, up to 19 carbon atoms;

alkoxy is O-alkyl;

$C_{1-6}$ alkoxy is alkoxy having 1, 2, 3, 4, 5, or 6 carbon atoms;

other ether substituents such as $CH_2OCH_3$, $(CH_2)_2OCH(CH_3)_2$, and the like;

thioether substituents including S-hydrocarbyl and other thioether substituents;

hydroxyhydrocarbyl, meaning hydrocarbyl-OH such as $CH_2OH$, $C(CH_3)_2OH$, etc, up to 19 carbon atoms;

nitrogen substituents such as $NO_2$, CN, and the like, including amino, such as $NH_2$, $NH(CH_2CH_3OH)$, $NHCH_3$, and the like;

$C_{0-6}$ amino is amino having 0, 1, 2, 3, 4, 5 or 6 carbon atoms;

carbonyl substituents, such as $CO_2H$, ester, amide, acyl, and the like;

acyl is —C(O)-hydrocarbyl;

halogen, such as chloro, fluoro, bromo, and the like fluorocarbyl, such as $CF_3$, $CF_2CF_3$, etc;

phosphorous substituents, such as $PO_3^{2-}$, and the like;

sulfur substituents, including S-hydrocarbyl, SH, $SO_3H$, $SO_2$-hydrocarbyl, $SO_3$-hydrocarbyl, and the like.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, $NO_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl. For this type of polycyclic ring system, an aromatic or heteroaromatic ring, not a non-aromatic ring, must be attached to the remainder of the molecule, i.e. the part of the molecule that is not B. In other words, in any structure depicting —B herein, where — is a bond, the bond is a direct bond to an aromatic ring.

In one embodiment, B is substituted aryl or heteroaryl.

In another embodiment B is substituted phenyl.

In another embodiment B has no halogen atoms.

In another embodiment B is 4-(1-hydroxy-2,2-dimethylpropyl)phenyl.

In another embodiment B is 4-(1-hydroxy-2-methylpropan-2-yl)phenyl.

In another embodiment B is 4-(1-hydroxy-2-methylpropyl)phenyl.

In another embodiment B is 4-(1-hydroxybutyl)phenyl.

In another embodiment B is 4-(1-hydroxyheptyl)phenyl.

In another embodiment B is 4-(1-hydroxyhexyl)phenyl.

In another embodiment B is 4-(1-hydroxypentyl)phenyl.

In another embodiment B is 4-(1-hydroxypropyl)phenyl.

In another embodiment B is 4-(3-hydroxy-2-methylheptan-2-yl)phenyl.

In another embodiment B is 4-(3-hydroxy-2-methyloctan-2-yl)phenyl.

In another embodiment B is 1-hydroxy-2,3-dihydro-1H-inden-5-yl.

In another embodiment B is 2,3-dihydro-1H-inden-5-yl.

In another embodiment B is 3-(hydroxy(1-propylcyclobutyl)methyl)phenyl.

In another embodiment B is 4-(1-hydroxy-5,5-dimethylhexyl)phenyl.

In another embodiment B is 4-(hydroxy(1-propylcyclobutyl)methyl)phenyl.

In another embodiment B is 4-tert-butylphenyl.

In another embodiment B is 4-hexylphenyl.

In another embodiment B is 4-(1-hydroxy-2-phenylethyl)phenyl.

In another embodiment B is 4-(1-hydroxy-3-phenylpropyl)phenyl.

In another embodiment B is 4-(1-hydroxycyclobutyl)phenyl.

In another embodiment B is 4-(2-cyclohexyl-1-hydroxyethyl)phenyl.

In another embodiment B is 4-(3-cyclohexyl-1-hydroxypropyl)phenyl.

In another embodiment B is 4-(cyclohexyl(hydroxy)methyl)phenyl.

In another embodiment B is 4-(cyclohexylmethyl)phenyl.

In another embodiment B is 4-(hydroxy(phenyl)methyl)phenyl.

In another embodiment B is phenyl substituted with $C_{1-10}$ acyl. $C_{1-10}$ acyl is acyl having from 1 to 10 carbon atoms.

Another embodiment is a compound according to the structure

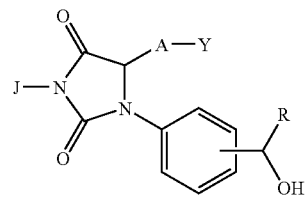

or a pharmaceutical salt thereof, or a prodrug thereof, wherein R is hydrogen or $C_{1-10}$ hydrocarbyl.

Another embodiment is a compound according to the structure

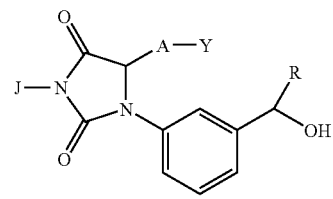

or a pharmaceutical salt thereof, or a prodrug thereof, wherein R is hydrogen or $C_{1-10}$ hydrocarbyl.

Another embodiment is a compound according to the structure

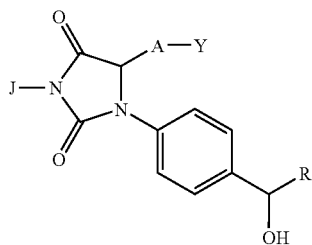

or a pharmaceutical salt thereof, or a prodrug thereof, wherein R is hydrogen or $C_{1-10}$ hydrocarbyl.

Another embodiment is a compound according to the structure

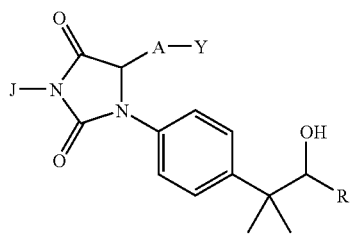

"$C_{1-10}$" hydrocarbyl is hydrocarbyl having 1, 2, 3, 4, 5, 6, 7, 8, 9, or 10 carbon atoms.

Hydrocarbyl is a moiety consisting of only carbon and hydrogen, and includes, but is not limited to alkyl, alkenyl, alkynyl, and the like, and in some cases aryl, and combinations thereof.

Alkyl is hydrocarbyl having no double or triple bonds including:
linear alkyl such as methyl, ethyl, propyl, n-butyl, n-pentyl, n-hexyl, and the like;
branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;
cycloalkyl such as cyclopropyl, cyclobutyl, cyclopentyl, cyclohexyl, cycloheptyl, etc.; and
alkyl fragments consisting of both cyclic and noncyclic components, whether linear or branched, which may be attached to the remainder of the molecule at any available position including terminal, internal, or ring carbon atoms.
$C_{1-6}$ alkyl is alkyl having 1, 2, 3, 4, 5, or 6 carbon atoms.
Alkenyl is hydrocarbyl having one or more double bonds including
linear alkenyl, branched alkenyl, cyclic alkenyl, and combinations thereof in analogy to alkyl.
Alkynyl is hydrocarbyl having one or more triple bonds including linear alkynyl, branched alkynyl, cyclic alkynyl and combinations thereof in analogy to alkyl.
Aryl is an unsubstituted or substituted aromatic ring or ring system such as phenyl, naphthyl, biphenyl, and the like. Aryl may or may not be hydrocarbyl, depending upon whether it has substituents with heteroatoms.
Arylalkyl is alkyl which is substituted with aryl. In other words alkyl connects aryl to the remaining part of the molecule.

Examples are —$CH_2$-Phenyl, —$CH_2$—$CH_2$-Phenyl, and the like. Arylalkyl may or may not be hydrocarbyl, depending upon whether the aryl portion has substituents with heteroatoms.
Unconjugated dienes or polyenes have one or more double bonds which are not conjugated. They may be linear, branched, or cyclic, or a combination thereof.
Combinations of the above are also possible.

Thus, each of the structures below is contemplated. These structures, or pharmaceutically acceptable salts thereof, or prodrugs thereof, individually represent a compound which is an embodiment contemplated herein. In other words, each structure represents a different embodiment.

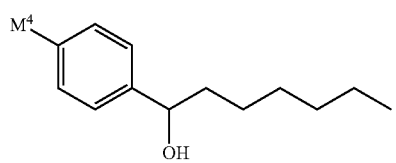

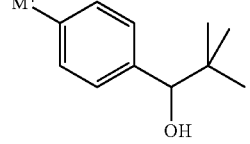

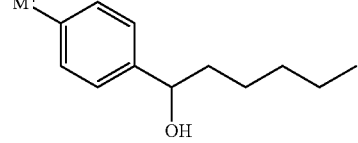

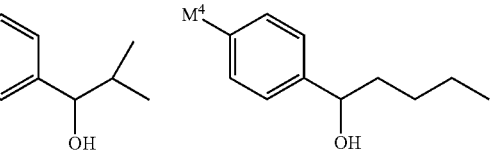

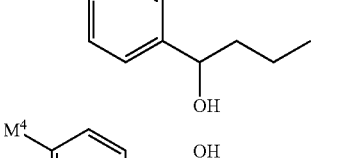

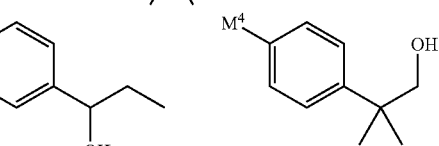

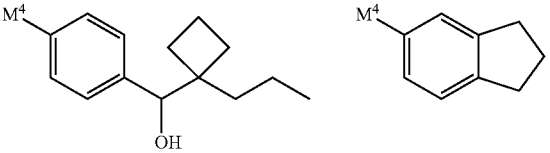

-continued
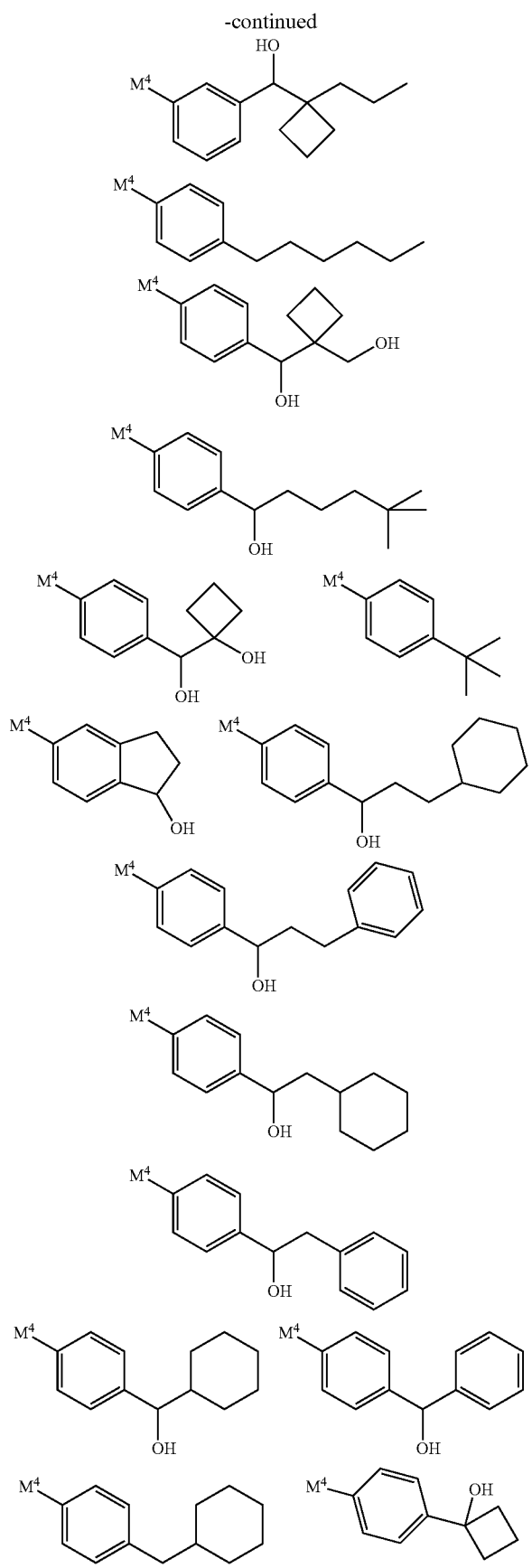
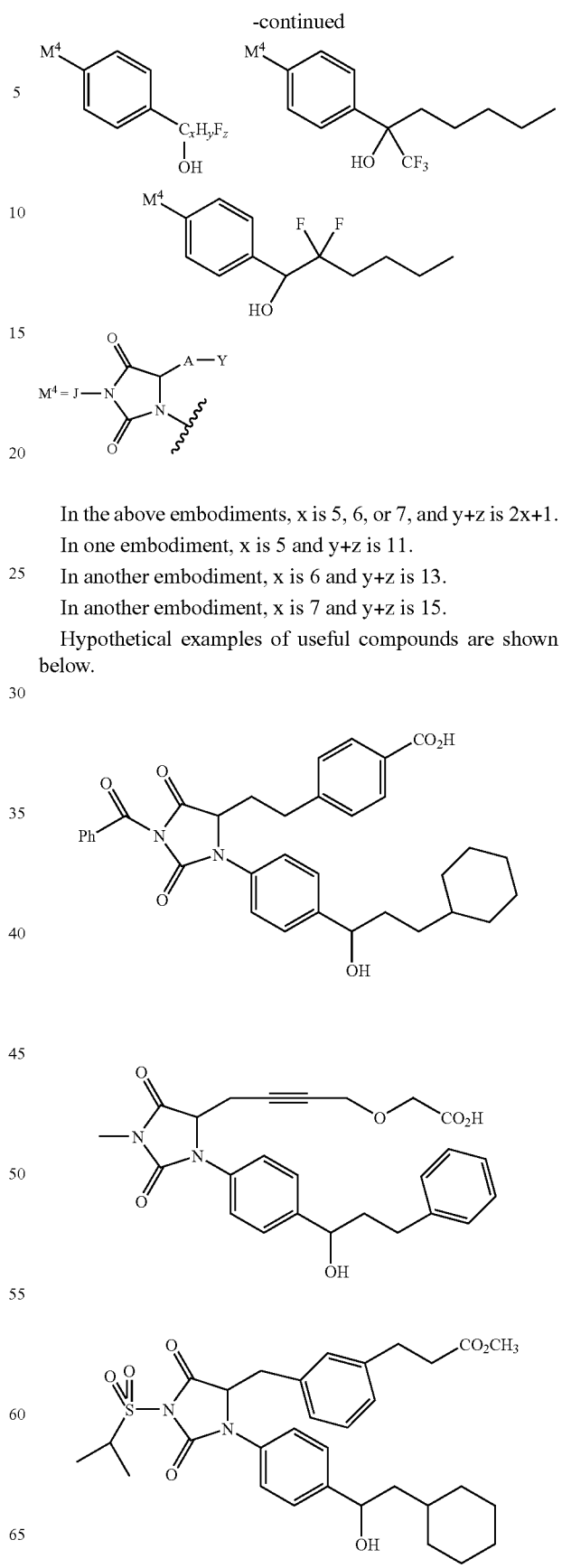
In the above embodiments, x is 5, 6, or 7, and y+z is 2x+1.
In one embodiment, x is 5 and y+z is 11.
In another embodiment, x is 6 and y+z is 13.
In another embodiment, x is 7 and y+z is 15.
Hypothetical examples of useful compounds are shown below.

-continued
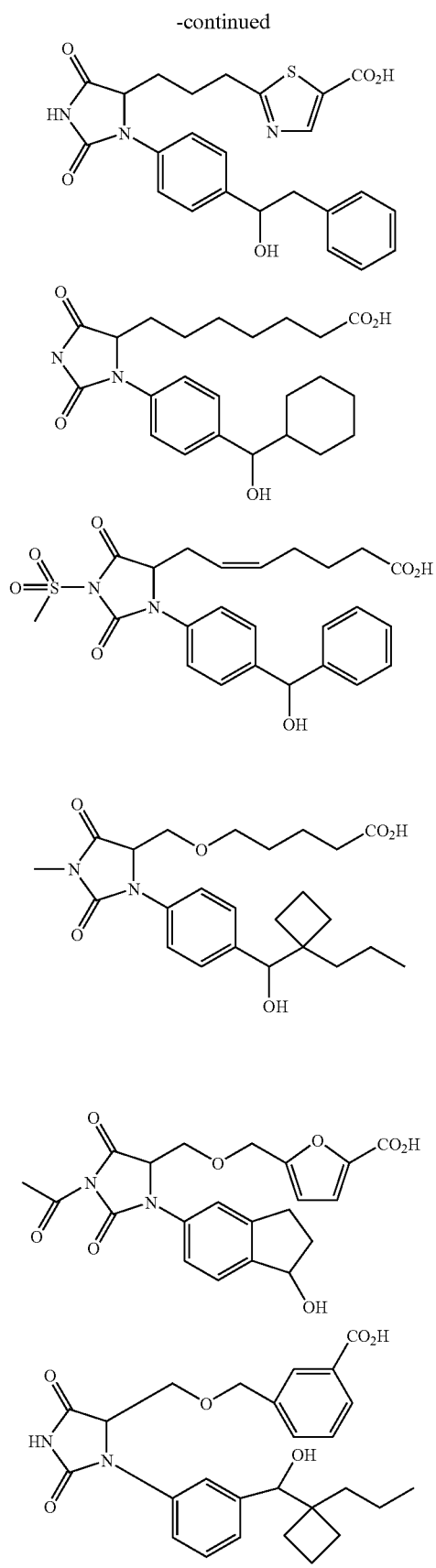
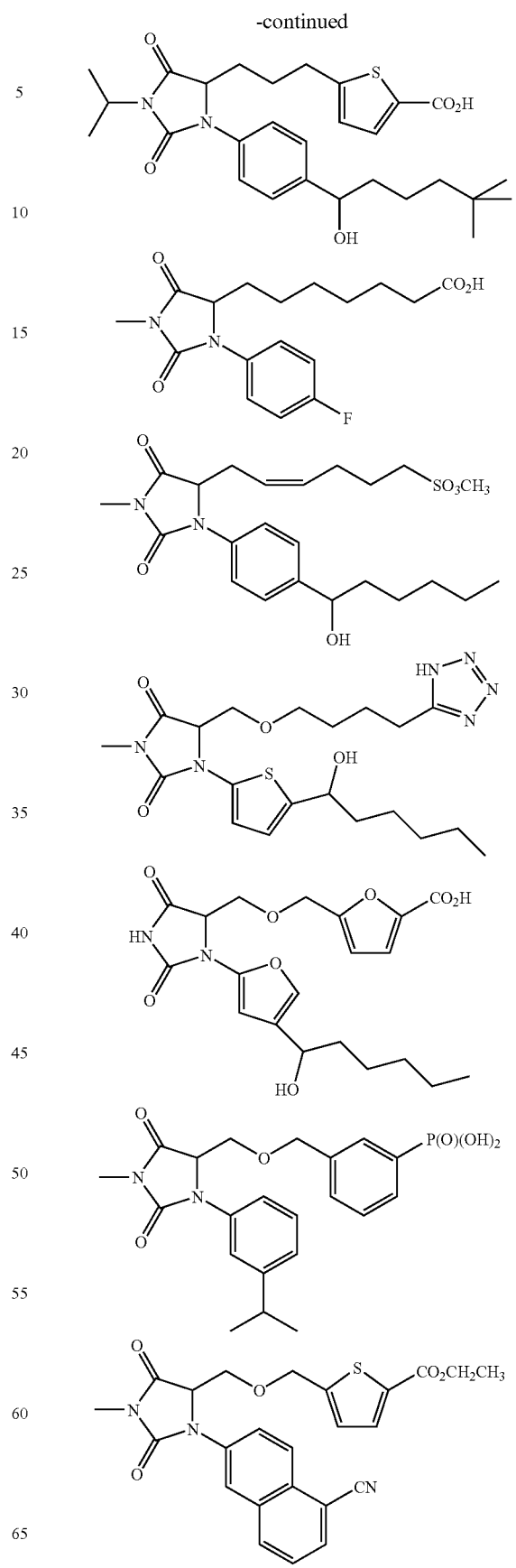

25
-continued
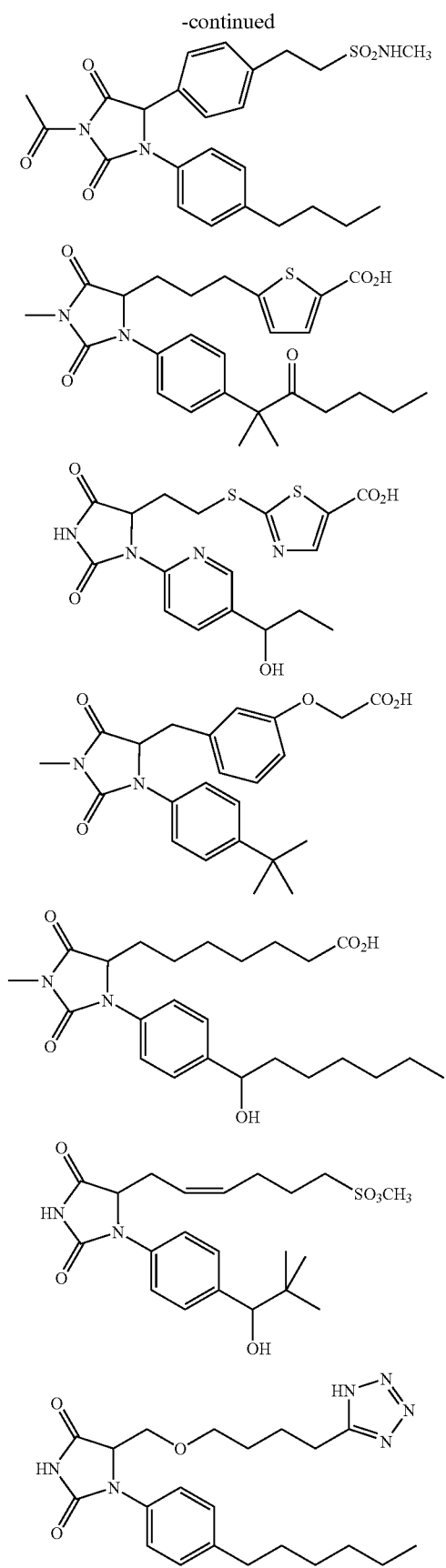
26
-continued
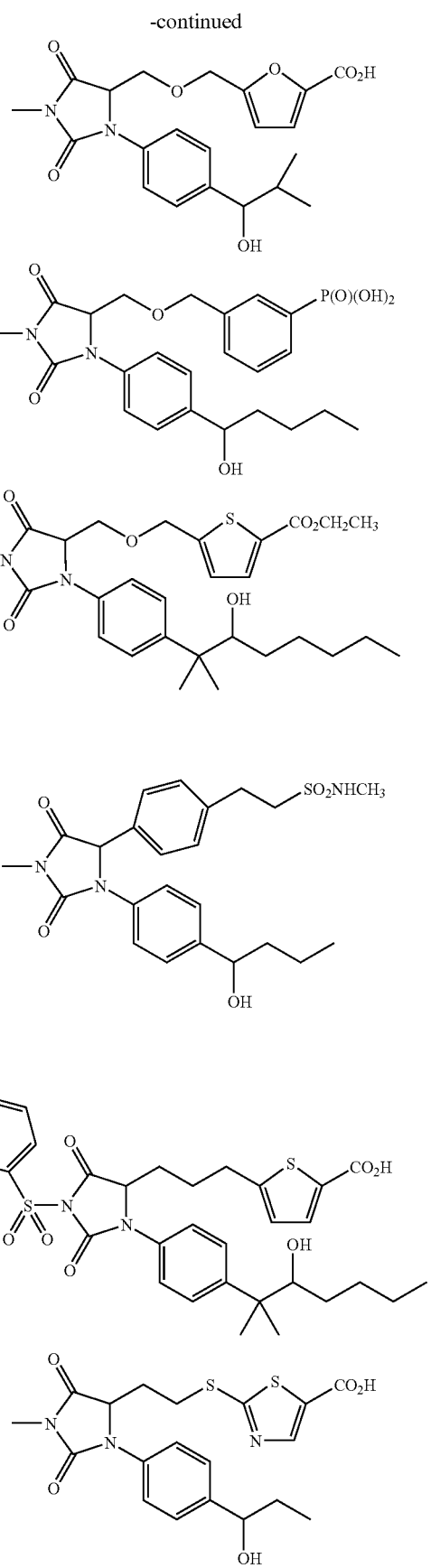

-continued

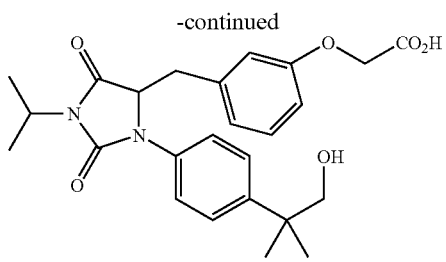

COMPOUND EXAMPLES

The following are hypothetical examples of useful compounds:

Compound Example 1

A compound having a structure

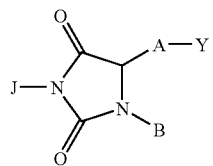

or a pharmaceutically acceptable salt thereof, or a prodrug thereof;
wherein a dashed line represents the presence or absence of a bond;
Y is an organic acid functional group, or an amide or ester thereof comprising up to 14 carbon atoms; or Y is hydroxymethyl or an ether thereof comprising up to 14 carbon atoms; or Y is a tetrazolyl functional group;
A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—;
J is H, $R^1$, $C(O)R^1$, or $SO_2R^1$; wherein $R^1$ is $C_{1-6}$ alkyl, phenyl, or biphenyl; and
B is aryl or heteroaryl.

Compound Example 2

The compound according to compound example 1 wherein Y is selected from $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

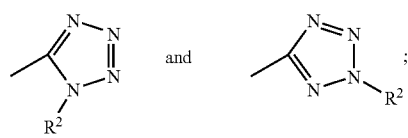

wherein $R^2$ is independently H, $C_1$-$C_6$ alkyl, unsubstituted phenyl, or unsubstituted biphenyl.

Compound Example 3

The compound according to compound example 1 or 2 wherein B is substituted phenyl.

Compound Example 4

The compound according to compound example 1 or 2 having a structure

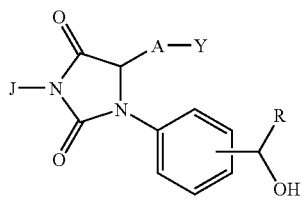

or a pharmaceutically acceptable salt thereof, or a prodrug thereof;
wherein R is hydrogen or $C_{1-10}$ hydrocarbyl.

Compound Example 5

The compound according to compound example 4 wherein R is alkyl.

Compound Example 6

The compound according to compound example 4 wherein R is arylalkyl.

Compound Example 7

The compound according to compound example any one of compound examples 1 to 6 having a structure

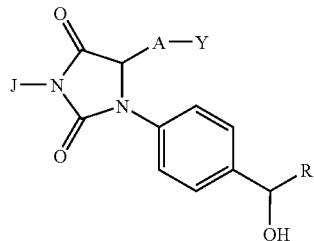

or a pharmaceutically acceptable salt thereof, or a prodrug thereof;
wherein R is hydrogen or $C_{1-10}$ hydrocarbyl.

Compound Example 8

The compound according to compound example 1 or 2 wherein A is (3-methylphenoxy)methyl.

Compound Example 9

The compound according to compound example 1 or 2 wherein A is (4-but-2-ynyloxy)methyl.

Compound Example 10

The compound according to compound example 1 or 2 wherein A is 2-(2-ethylthio)thiazol-4-yl.

Compound Example 11

The compound according to compound example 1 or 2 wherein A is 2-(3-propyl)thiazol-5-yl.

Compound Example 12

The compound according to compound example 1 or 2 wherein A is 3-methoxymethyl)phenyl.

Compound Example 13

The compound according to compound example 1 or 2 wherein A is 3-(3-propylphenyl.

Compound Example 14

The compound according to compound example 1 or 2 wherein A is 3-methylphenethyl.

Compound Example 15

The compound according to compound example 1 or 2 wherein A is 4-(2-ethyl)phenyl.

Compound Example 16

The compound according to compound example 1 or 2 wherein A is 4-phenethyl.

Compound Example 17

The compound according to compound example 1 or 2 wherein A is 4-methoxybutyl.

Compound Example 18

The compound according to compound example 1 or 2 wherein A is 5-(methoxymethyl)furan-2-yl.

Compound Example 19

The compound according to compound example 1 or 2 wherein A is 5-(methoxymethyl)thiophen-2-yl.

Compound Example 20

The compound according to compound example 1 or 2 wherein A is 5-(3-propyl)furan-2-yl.

Compound Example 21

The compound according to compound example 1 or 2 wherein A is 5-(3-propyl)thiophen-2-yl.

Compound Example 22

The compound according to compound example 1 or 2 wherein A is 6-hexyl.

Compound Example 23

The compound according to compound example 1 or 2 wherein A is (Z)-6-hex-4-enyl.

Compound Example 24

The compound according to any one of compound examples 1, 2, and 8-23 wherein B is 4-(1-hydroxy-2,2-dimethylpropyl)phenyl.

Compound Example 25

The compound according to any one of compound examples 1, 2, and 8-23 wherein B is 4-(1-hydroxy-2-methylpropan-2-yl)phenyl.

Compound Example 26

The compound according to any one of compound examples 1, 2, and 8-23 wherein B is 4-(1-hydroxy-2-methylpropyl)phenyl.

Compound Example 27

The compound according to any one of compound examples 1, 2, and 8-23 wherein B is 4-(1-hydroxybutyl)phenyl.

Compound Example 28

The compound according to any one of compound examples 1, 2, and 8-23 wherein B is 4-(1-hydroxyheptyl)phenyl.

Compound Example 29

The compound according to any one of compound examples 1, 2, and 8-23 wherein B is 4-(1-hydroxyhexyl)phenyl.

Compound Example 30

The compound according to any one of compound examples 1, 2, and 8-23 wherein B is 4-(1-hydroxypentyl)phenyl.

Compound Example 31

The compound according to any one of compound examples 1, 2, and 8-23 wherein B is 4-(1-hydroxypropyl)phenyl.

Compound Example 32

The compound according to any one of compound examples 1, 2, and 8-23 wherein B is 4-(3-hydroxy-2-methylheptan-2-yl)phenyl.

Compound Example 33

The compound according to any one of compound examples 1, 2, and 8-23 wherein B is 4-(3-hydroxy-2-methyloctan-2-yl)phenyl.

Compound Example 34

The compound according to any one of compound examples 1, 2, and 8-23 wherein B is 1-hydroxy-2,3-dihydro-1H-inden-5-yl.

Compound Example 35

The compound according to any one of compound examples 1, 2, and 8-23 wherein B is 2,3-dihydro-1H-inden-5-yl.

Compound Example 36

The compound according to any one of compound examples 1, 2, and 8-23 wherein B is 3-(hydroxy(1-propylcyclobutyl)methyl)phenyl.

Compound Example 37

The compound according to any one of compound examples 1, 2, and 8-23 wherein B is 4-(1-hydroxy-5,5-dimethylhexyl)phenyl.

Compound Example 38

The compound according to any one of compound examples 1, 2, and 8-23 wherein B is 4-(hydroxy(1-propylcyclobutyl)methyl)phenyl.

Compound Example 39

The compound according to any one of compound examples 1, 2, and 8-23 wherein B is 4-tert-butylphenyl.

Compound Example 40

The compound according to any one of compound examples 1, 2, and 8-23 wherein B is 4-hexylphenyl.

Compound Example 41

The compound according to any one of compound examples 1, 2, and 8-23 wherein B is 4-(1-hydroxy-2-phenylethyl)phenyl.

Compound Example 42

The compound according to any one of compound examples 1, 2, and 8-23 wherein B is 4-(1-hydroxy-3-phenylpropyl)phenyl.

Compound Example 43

The compound according to any one of compound examples 1, 2, and 8-23 wherein B is 4-(1-hydroxycyclobutyl)phenyl.

Compound Example 44

The compound according to any one of compound examples 1, 2, and 8-23 wherein B is 4-(2-cyclohexyl-1-hydroxyethyl)phenyl.

Compound Example 45

The compound according to any one of compound examples 1, 2, and 8-23 wherein B is 4-(3-cyclohexyl-1-hydroxypropyl)phenyl.

Compound Example 46

The compound according to any one of compound examples 1, 2, and 8-23 wherein B is 4-(cyclohexyl(hydroxy)methyl)phenyl.

Compound Example 47

The compound according to any one of compound examples 1, 2, and 8-23 wherein B is 4-(cyclohexylmethyl)phenyl.

Compound Example 48

The compound according to any one of compound examples 1, 2, and 8-23 wherein B is 4-(hydroxy(phenyl)methyl)phenyl.

Compound Example 49

The compound according to any one of compound examples 1 to 48 wherein $R^1$ is $C_{1-3}$ alkyl.

Compound Example 50

The compound according to any one of compound examples 1 to 48 wherein $R^1$ is phenyl.

Compound Example 51

The compound according to any one of compound examples 1 to 48 wherein $R^1$ is biphenyl.

Compound Example 52

The compound according to any one of compound examples 1 to 48 wherein J is hydrogen.

Compound Example 53

The compound according to any one of compound examples 1 to 48 wherein J is methyl.

Compound Example 54

The compound according to any one of compound examples 1 to 51 wherein J is $R^1$.

Compound Example 55

The compound according to any one of compound examples 1 to 51 wherein J is $C(O)R^1$.

Compound Example 56

The compound according to any one of compound examples 1 to 51 wherein J is $SO_2R^1$.

Compound Example 57

The compound according to any one of compound examples 1, and 24 to 57 wherein A is —$CH_2CH_2A^1$- or —$CH_2OA^1$-, wherein $A^1$ is linear $C_4H_8$, $C_3H_6O$, or $C_3C_6S$; —$CH_2$—Ar—; —O—Ar—; —S—Ar—; —Ar—$CH_2$—; —Ar—O—; —Ar—S—, or Ar; with the proviso that A does not contain —O—O—, —S—O—, or O—S.

The following are hypothetical examples of compositions, kits, methods, uses, and medicaments employing the hypothetical compound examples.

Composition Example

A composition comprising a compound according to any one of compound examples 1 to 58, wherein said composition is a liquid which is ophthalmically acceptable.

Medicament Examples

Use of a compound according to any one of compound examples 1 to 58 in the manufacture of a medicament for the treatment of glaucoma or ocular hypertension in a mammal.

Use of a compound according to any one of compound examples 1 to 58 in the manufacture of a medicament for the treatment of baldness in a person.

A medicament comprising a compound according to any one of compound examples 1 to 58, wherein said composition is a liquid which is ophthalmically acceptable.

Method Example

A method comprising administering a compound according to any one of compound examples 1 to 58 to a mammal for the treatment of glaucoma or ocular hypertension.

Kit Example

A kit comprising a composition comprising compound according to any one of compound examples 1 to 58, a container, and instructions for administration of said composition to a mammal for the treatment of glaucoma or ocular hypertension.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjuvants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

For treatment of diseases affecting the eye including glaucoma, these compounds can be administered topically, periocularly, intraocularly, or by any other effective means known in the art.

Synthetic Methods

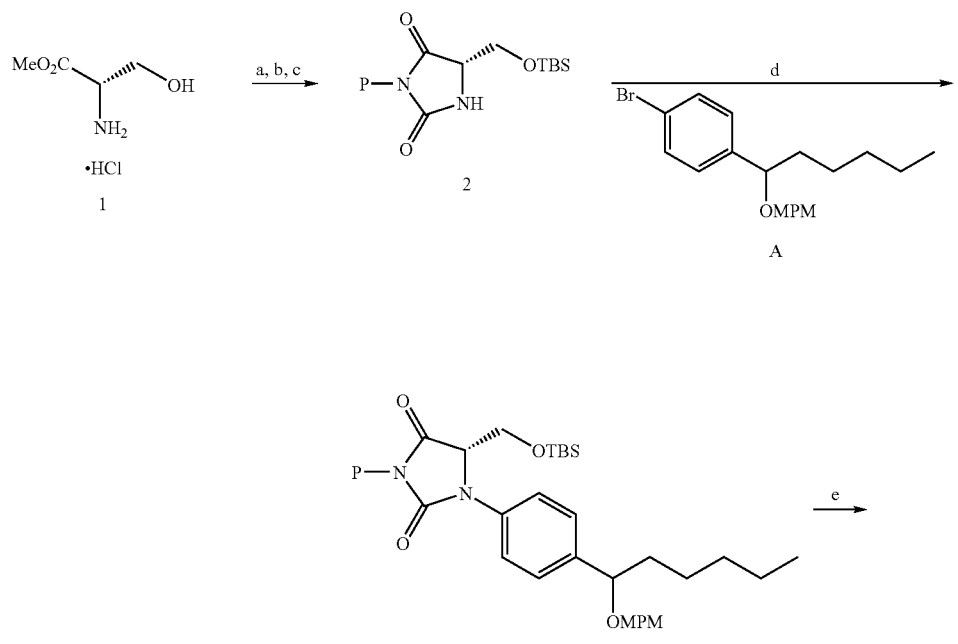

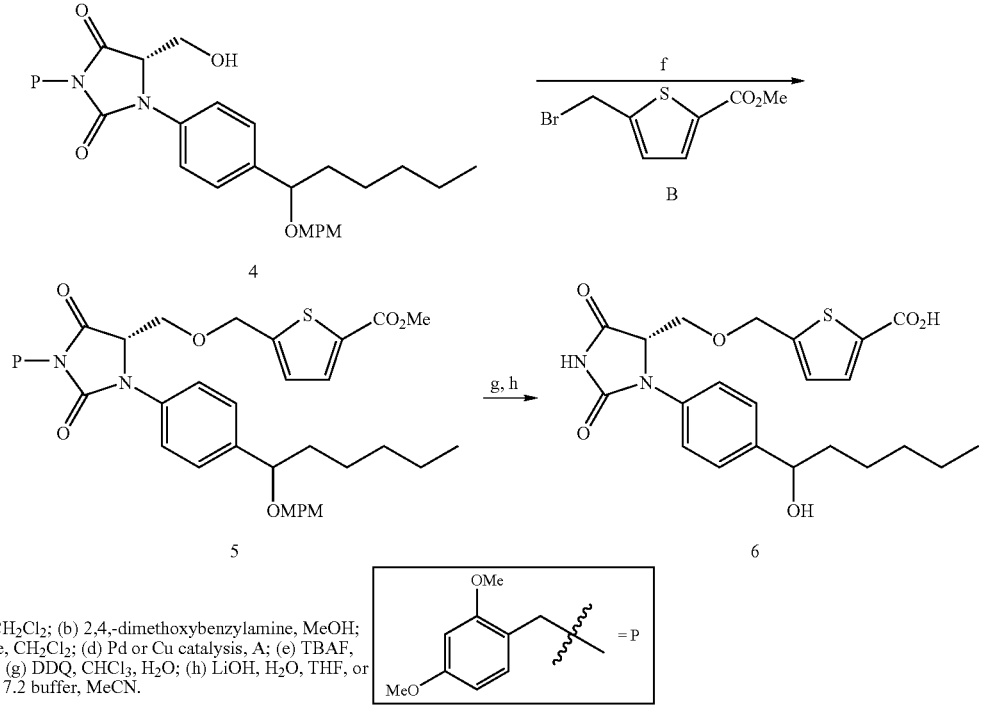

(a) TBSCl, imidazole, CH$_2$Cl$_2$; (b) 2,4,-dimethoxybenzylamine, MeOH; (c) triphosgene, pyridine, CH$_2$Cl$_2$; (d) Pd or Cu catalysis, A; (e) TBAF, THF; (f) B, NaH, DMF; (g) DDQ, CHCl$_3$, H$_2$O; (h) LiOH, H$_2$O, THF, or rabbit liver esterase, pH 7.2 buffer, MeCN.

While there are many ways to prepare the compounds disclosed herein, one exemplary synthesis may begin with L-serine methyl ester hydrochloride (1, see Scheme 1). Sequential silylation, amide formation and cyclization with triphosgene provides hydantoin 2 according to the procedures of Zhang, et al., *J. Org. Chem.* 2006, 71, 1750-1753. The dimethoxybenzylamide is chosen for its ease of deprotection under mild oxidative conditions, but many other protecting groups may be useful in this regard. Palladium- or copper-catalyzed reaction of 2 with bromide A gives arylated product 3 according to the procedures of Buchwald (for Cu, see *J. Am. Chem. Soc.* 2002, 124, 7421-7428; for Pd, see *Org. Lett.* 2000, 2, 1101-1104). A wide variety of substituted bromophenyl and other bromoaryl analogs of A may be employed. The haloarenes A are either available commercially or may be made according to published literature procedures. For example, U.S. patent application Ser. No. 11/009,298, filed on Dec. 10, 2004 and U.S. Provisional Patent Application 60/742,779 filed on Dec. 6, 2005, both of which are expressly incorporated by reference herein, disclose methods of making a number of useful substituted bromophenyl compounds. These procedures may also be readily adapted to other bromoaryl compounds such as substituted bromothienyl, substituted bromofuryl, substituted bromopyridinyl, substituted bromonaphthyl, substituted bromobenzothienyl, and the like. Deprotection of 3 gives alcohol 4. Alkylation of 4 with bromide B (prepared according to the procedure of U.S. Provisional Patent Application No. 60/804,680, filed on Jun. 14, 2006, expressly incorporated by reference herein) gives ester 5. Similar procedures may be carried out by substituting the thienyl of B with phenyl (i.e. X—CH$_2$-phenyl-CO$_2$H) or another heteroaromatic ring such as furyl, pyridinyl, etc. These compounds are commercially available, or may be readily prepared by art recognized methods. Deprotection of 5 using an oxidant such as DDQ or CAN, followed by saponification affords the target compound 6.

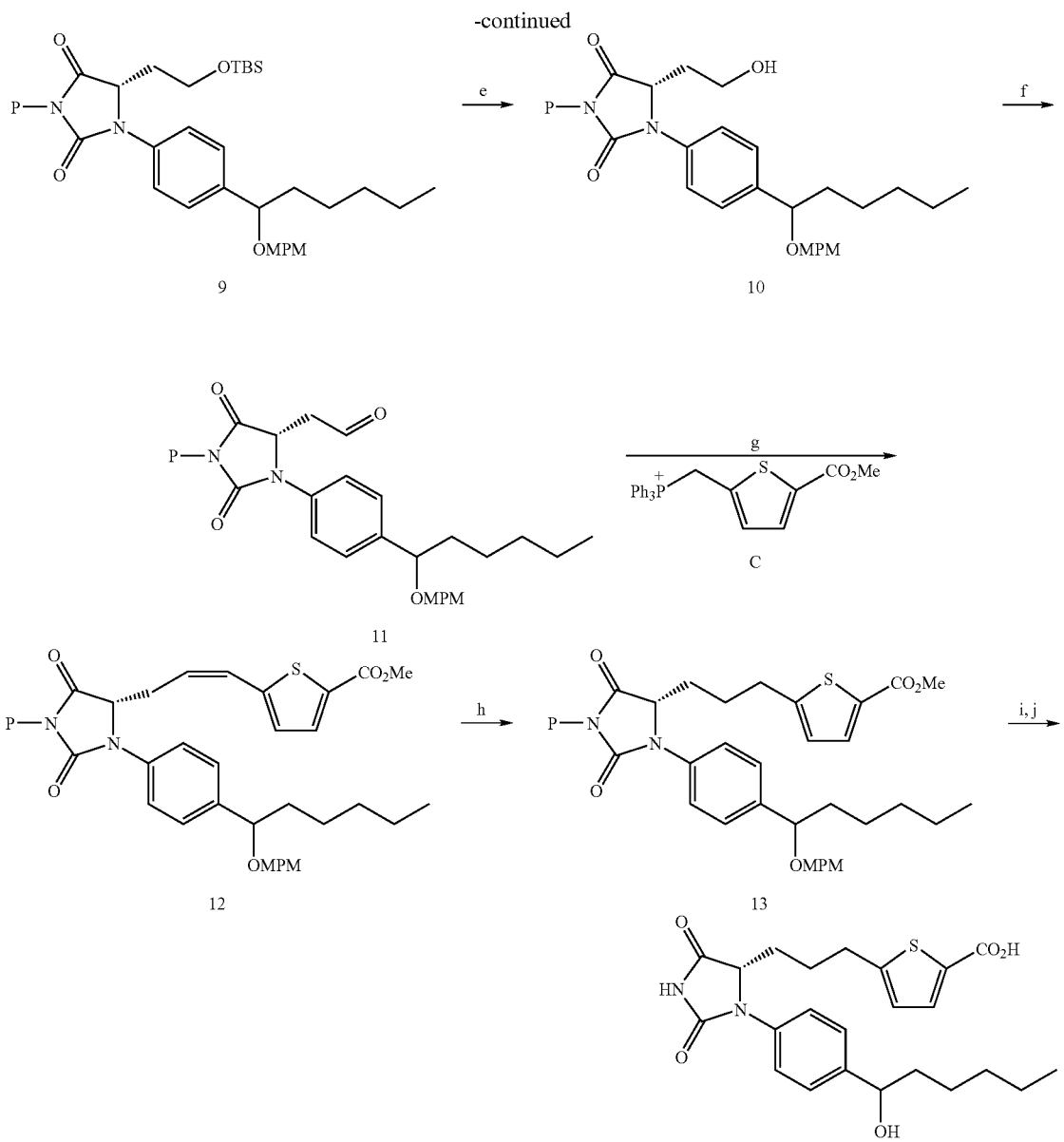

(a) TBSCl, imidazole, CH$_2$Cl$_2$; (b) 2,4,-dimethoxybenzylamine, MeOH; (c) triphosgene, pyridine, CH$_2$Cl$_2$;
(d) Pd or Cu catalysis, A; (e) TBAF, THF; (f) Swern oxidation; (g) K$_2$CO$_3$, C, DMF; (h) H$_2$, Pd/C, MeOH;
(i) DDQ, CHCl$_3$, H$_2$O; (j) LiOH, H$_2$O, THF, or rabbit liver esterase, pH 7.2 buffer, MeCN.

Analogous to scheme 1, another hypothetical route to the target compounds begins with L-homoserine methyl ester 7 (derived from commercially available L-homoserine). Protection, amide formation and cyclization affords hydantoin 8 according to the Zhang precedent (see scheme 2). Palladium- or copper-catalyzed reaction of 8 with bromide A gives arylated product 9. Deprotection affords alcohol 10 and oxidation affords aldehyde 11. Wittig reaction of 11 with phosphonate C (see *Collect. Czech. Chem. Commun.* 1994, 58, 138-148) affords alkene 12. A variety of analogs of phosphonate C are known in the literature (e.g., *Collect. Czech. Chem. Commun.* 1994, 59, 2533-2544). Hydrogenation, deprotection and saponification affords the target compound 14.

Scheme 3

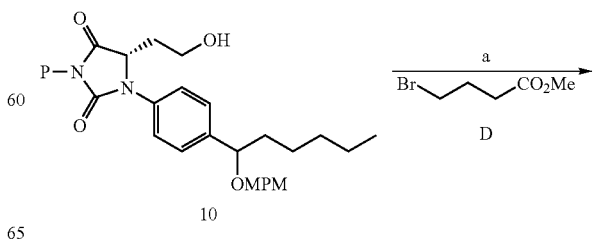

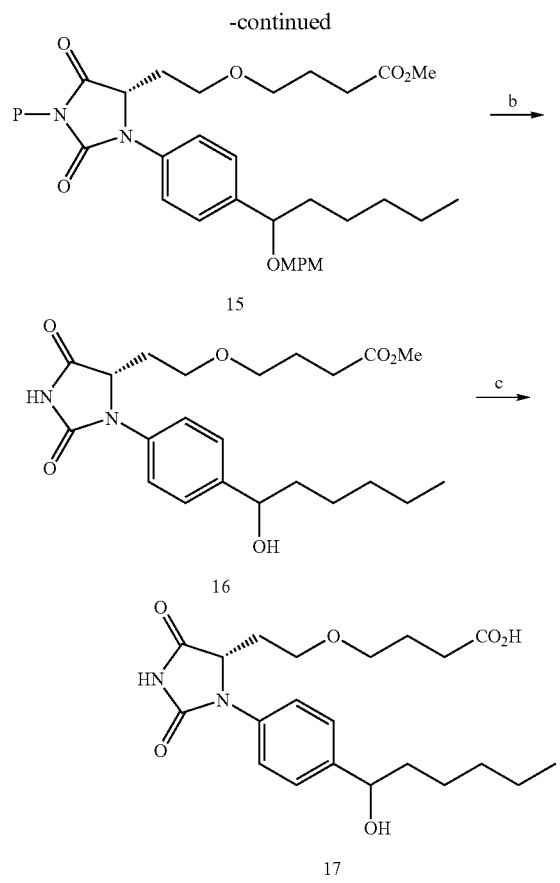

(a) D, NaH, DMF;
(b) DDQ, CHCl₃, H₂O;
(c) LiOH, H₂O, THF, or rabbit liver esterase, pH 7.2 buffer, MeCN.

Ethers in the carboxylate top chain are also envisioned. Thus, alkylation of alcohol 10 with bromide D affords ether 15 (see scheme 3). A variety of analogs of electrophile D are known in the literature and may be employed in place of D. Deprotection and saponification give target compound 17.

Scheme 4

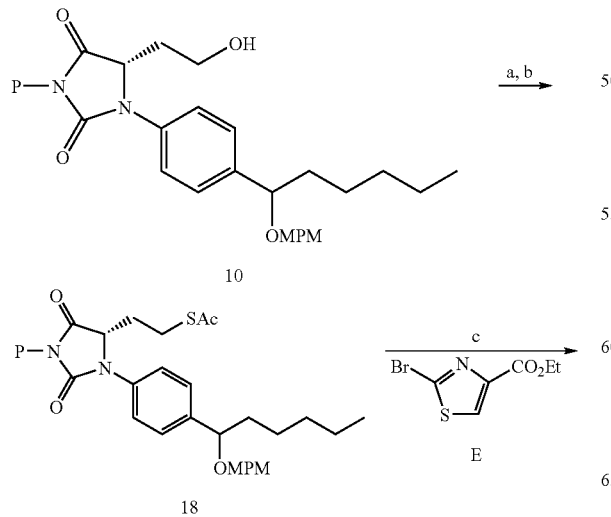

(a) MsCl, Et₃N, CH₂Cl₂; (b) KSAc, DMF; (c) E, K₂CO₃, PBu₃, EtOH;
(d) DDQ, CHCl₃, H₂O;
(e) LiOH, H₂O, THF, or rabbit liver esterase, pH 7.2 buffer, MeCN.

Compounds which replace the oxygen atom in a compound such as 17 with sulfur are also envisioned (see scheme 4). Thus, alcohol 10 is converted to thioacetate 18 and arene 19 using electrophile E according to the methods of Tani et al., US 2005/0124577, which is incorporated by reference herein. Ester saponification gives target compound 20. A variety of analogs of electrophile E are known in the literature and may be employed in place of E (e.g. see Tani, et al.). Electrophile E may or may not be aromatic or heteroaromatic.

Scheme 5

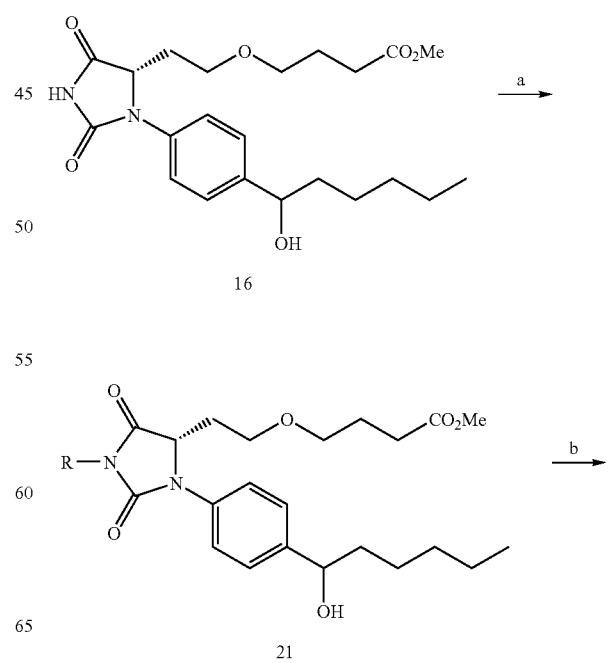

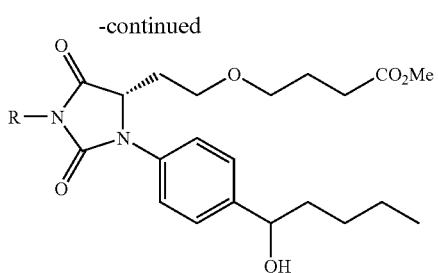

22

(a) alkylation: ROH, PPh₃, DEAD, THF or RX, Na₂CO₃, acetone, H₂O; acylation: R'C(O)Cl or R'SO₂Cl, pyridine, CHCl₃; (b) rabbit liver esterase, pH 7.2 buffer, MeCN.

Compounds with substituents on the imide nitrogen atom are also envisioned. Substitution at N-3 of a compound such as 16 takes place using a Mitsunobu reaction (e.g. see Alcaraz et al *Bioorg. Med. Chem. Lett.* 2003, 13, 4043-4046) or a mild alkylation or acylation procedure (e.g. see Meusel et al. *J. Org. Chem.* 2003, 68, 4684-4692 and Muccioli et al. *J. Med. Chem.* 2006, 49, 872-882) to give compound 21. A selective ester saponification then provides target compound 22. Alternatively, the desired group at N-3 can be introduced in the second step of scheme 1 or scheme 2 (replacing 2,4-dimethoxybenzylamine with the desired substituted amine).

U.S. Pat. No. 4,486,443 and U.S. Pat. No. 7,041,693 also provide methods for preparing hydantoins that can be applied to the compounds disclosed herein.

An alternative approach to that shown in Scheme 2 is shown in scheme 6.

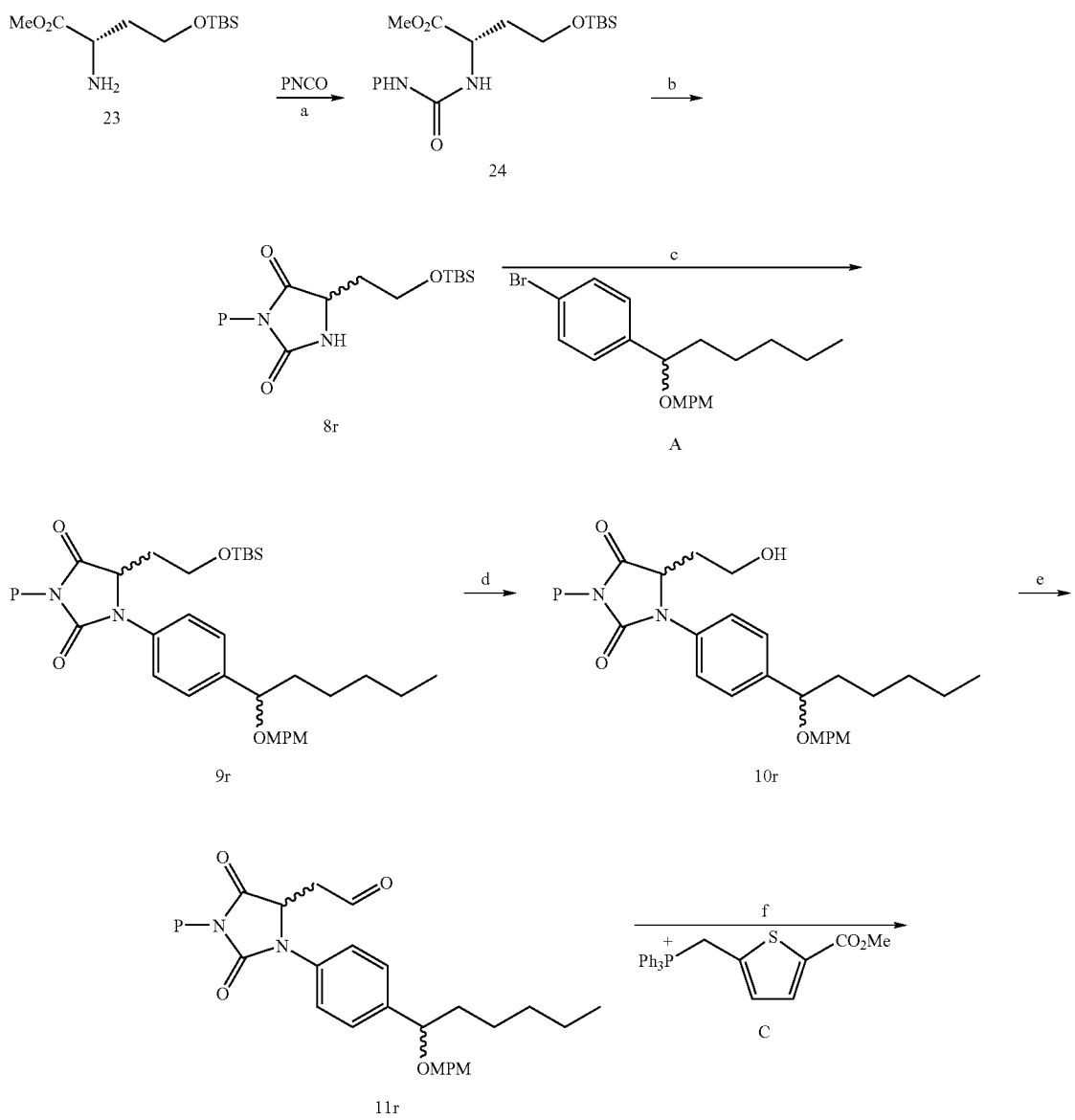

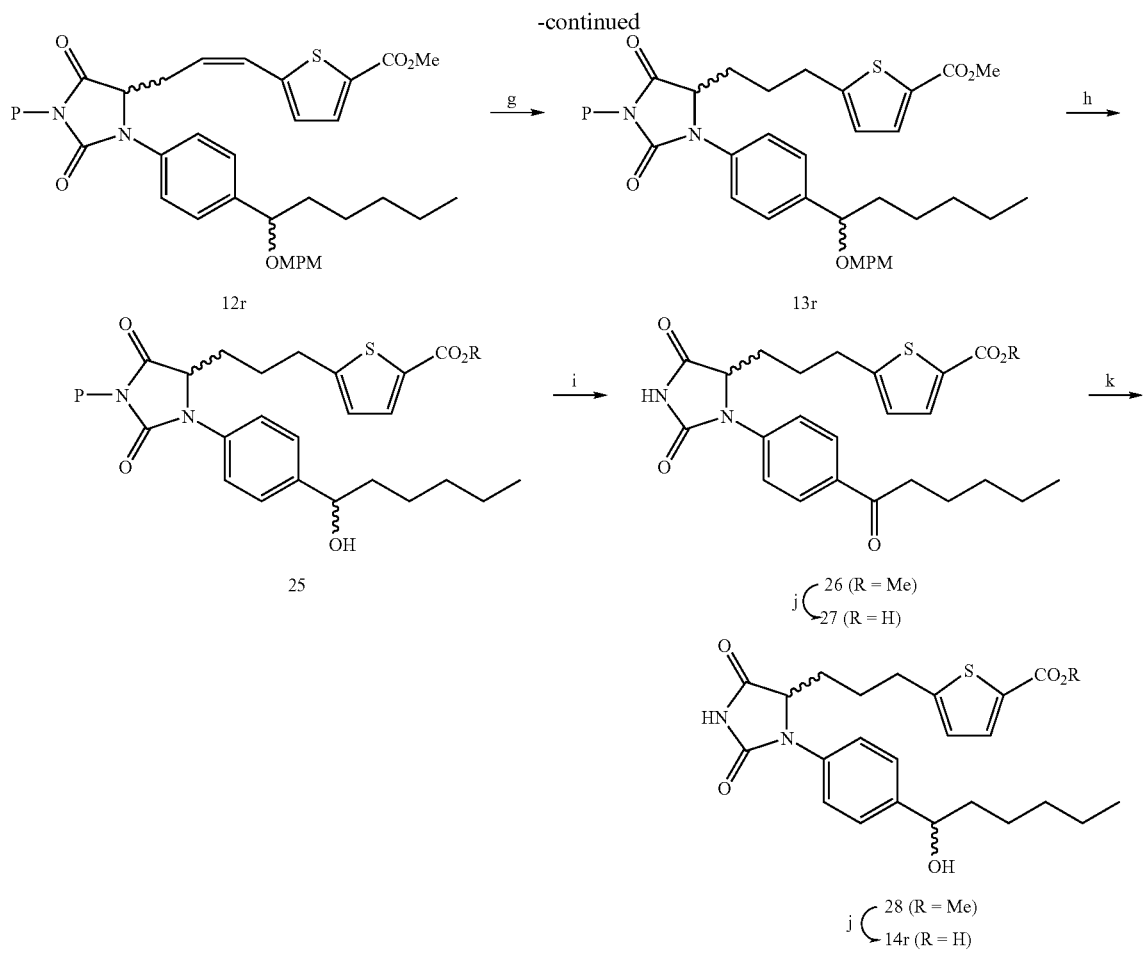

(a) 2,4-dimethoxybenzyl isocyanate, Et(i-Pr)$_2$N, CH$_2$Cl$_2$; (b) NaH, THF; (c) A, Pd$_2$(dba)$_3$, Xantphos, Cs$_2$CO$_3$, dioxane, reflux; (d) TBAF, THF; (e) Swern oxidation; (f) K$_2$CO$_3$, C, DMF; (g) H$_2$, Pd/C, EtOAc; (h) DDQ, CHCl$_3$, H$_2$O; (i) CAN, H$_2$O, MeCN; (j) LiOH, H$_2$O, THF; (k) NaBH$_4$, MeOH, CH$_2$Cl$_2$.

Example 1

5-(3-(3-(4-hexanoylphenyl)-2,5-dioxoimidazolidin-4-yl)propyl)thiophene-2-carboxylic acid (27)

Step 1. Addition of 23 to PNCO to Give 24

A solution of amino acid 23 (see Kline, T., et al. *J. Med. Chem.* 2002, 45, 3112-3129; 12.35 g, 49.9 mmol) and diisopropylethylamine (12.9 g, 99.8 mmol) in CH$_2$Cl$_2$ (100 mL) was added over 30 min to a solution of 2,4-dimethoxybenzyl isocyanate (see Trost and Fandrick, *Org. Lett.* 2005, 7, 823-826; 9.65 g, 49.9 mmol) in CH$_2$Cl$_2$ (100 mL) at room temperature. After stirring 1 h, the reaction mixture was diluted with CH$_2$Cl$_2$ (100 mL) and washed with water (2×150 mL), brine (150 mL), filtered through filter paper and concentrated in vacuo to afford 22 g of an oil. This oil was dissolved in hot hexane (250 mL) and stirred at room temperature overnight. The precipitated solid was collected by filtration. After drying under vacuum, 12.5 g of solid 24 was obtained which was shown by HPLC to be approximately 86% pure. The filtrate was concentrated to afford 9.5 g of an oil. This oil was purified by flash chromatography on 150 g silica gel (CH$_2$Cl$_2$→15% EtOAc/CH$_2$Cl$_2$, gradient) to afford 1.8 g of 24 as an oil that was shown by HPLC to be approximately 90% pure. The two samples of impure 24 were combined and purified by flash chromatography on 150 g silica gel (CH$_2$Cl$_2$→20% EtOAc/CH$_2$Cl$_2$, gradient) to afford 12.4 g (56%) of 24 as an oil that solidified on standing.

Step 2. Cyclization of 24 to Give 8r

Sodium hydride (75 mg, 3.1 mmol) was added in one portion to a solution of urea 24 (12.3 g, 27.9 mmol) in THF (150 mL) at room temperature. After 15 min the reaction mixture was diluted with EtOAc (150 mL), washed with water (2×100 mL) and brine (100 mL), filtered through filter paper and concentrated to afford 11 g of an oil. This oil was purified by flash chromatography on 125 g silica gel (CH$_2$Cl$_2$→10% EtOAc/CH$_2$Cl$_2$, gradient) to afford, after drying in vacuo 8.8 g (77%) of 8r as a solid. This material showed an optical rotation of 0° and is presumed to be racemic.

Step 3. Arylation of 8r with A to Give 9r

Pd$_2$(dba)$_3$ (41 mg, 0.045 mmol), Xantphos (77 mg, 0.133 mmol) and Cs$_2$CO$_3$ (428 mg, 1.31 mmol) were added sequentially to a solution of 8r (450 mg, 1.10 mmol) and bromoarene A (see Old and Dinh, WO2006/098918, incorporated by reference herein; 372 mg, 0.99 mmol) in 1,4-dioxane (7.1 mL). The flask was fitted with a reflux condenser, evacuated and refilled with nitrogen (5×) then heated at reflux. After 18 h, the reaction was cooled, diluted with EtOAc (75 mL) and filtered through celite, washing with excess EtOAc. The EtOAc filtrate was concentrated in vacuo. The crude residue was purified on 120 g silica gel (hexanes→25% EtOAc/hexanes, gradient) to afford 630 mg (91%) of 9r.

Step 4. Deprotection of 9r to Give 10r

Tetrabutylammonium fluoride (2.7 mL of a 1.0 M solution in THF, 2.7 mmol) was added to a solution of 9r (630 mg, 0.89 mmol) in THF (6 mL) at 0° C. The cooling bath was removed and the reaction was allowed to stir at room temperature overnight. After 18 h at room temperature the reaction was concentrated in vacuo. Water (50 mL) was added and the mixture was extracted with EtOAc (3×80 mL). The combined extracts were washed with brine (50 mL), dried ($Na_2SO_4$), filtered and concentrated in vacuo. The crude residue was purified on 40 g silica (hexanes→60% EtOAc/hexanes, gradient) to afford 465 mg (88%) of 10r.

Step 5. Oxidation of 10r to Give 11r

DMSO (69 µL, 0.97 mmol) was added to a solution of oxalyl chloride (234 µL of a 2.0 M solution in $CH_2Cl_2$, 0.47 mmol) and $CH_2Cl_2$ (3.3 mL) at −78° C. After 15 min at −78° C., a solution of 10r (230 mg, 0.39 mmol) in $CH_2Cl_2$ (1.1 mL) was added via cannula. After 15 at −78° C., triethylamine (434 µL, 3.11 mmol) was added. After 15 min, the reaction was allowed to warm to 0° C. After 30 min at room temperature, the reaction was allowed to warm to room temperature then saturated aqueous $NaHCO_3$ (30 mL) was added. The mixture was extracted with $CH_2Cl_2$ (3×50 mL), then dried ($Na_2SO_4$), filtered and concentrated in vacuo. Crude 11r was taken on to the next step without further purification.

Step 6. Reaction of 11r with C to Give 12r

Potassium carbonate (99.99%, 538 mg, 3.90 mmol) was added to crude 11r (~0.39 mmol) and phosphonate C (see *Collect. Czech. Chem. Commun.* 1994, 58, 138-148; 200 mg, 0.40 mmol) in DMF (3.9 mL) at room temperature. The reaction mixture was stirred at room temperature for 3 d then diluted with water (30 mL) and extracted with EtOAc (150 mL). The organic phase was washed with water (2×50 mL) and brine (50 mL) then dried ($Na_2SO_4$), filtered and concentrated in vacuo. The crude residue was purified on 40 g silica (hexanes→50% EtOAc/hexane, gradient) to afford 163 mg (58% over 2 steps) of 12r as a mixture of cis- and trans-olefins.

Step 7. Hydrogenation of 12r to Give 13r

Palladium on carbon (10 wt. %, 40 mg) was added to a solution of 12r (163 mg, 0.22 mmol) in EtOAc (2.2 mL). A hydrogen atmosphere was established by evacuating and refilling with hydrogen (5×) and the reaction mixture was stirred under a balloon of hydrogen for 18 h. The reaction mixture was filtered through celite, washing with EtOAc, and the filtrate was concentrated in vacuo to afford 150 mg (92%) of saturated compound 13r.

Step 8. Deprotection of 13r to Give 25

2,3-Dichloro-5,6-dicyano-1,4-benzoquinone (DDQ, 43 mg, 0.19 mmol) was added to a mixture of 13r (66 mg, 0.09 mmol) in $CHCl_3$ (0.95 mL) and water (0.05 mL) at room temperature. After 1 h at room temperature, the reaction was quenched with saturated aqueous $NaHCO_3$ (10 mL) and extracted with EtOAc (3×15 mL). The combined extracts were washed with saturated aqueous $NaHSO_3$ (10 mL) and brine (10 mL) then dried ($Na_2SO_4$), filtered and concentrated in vacuo. The crude residue was purified on 4 g silica (hexanes→60% EtOAc/hexanes, gradient) to afford 44 mg (80%) of alcohol 25.

Step 9. Oxidative Deprotection of 25 to Give 26

Water (0.03 mL) and ammonium cerium(IV) nitrate (CAN, 20 mg, 0.036 mmol) were added to a solution of 25 (9 mg, 0.015 mmol) in MeCN (0.3 mL). After 1 h at room temperature, the reaction mixture was heated at 50° C. After 2 h at 50° C., the mixture was cooled to room temperature and quenched with saturated aqueous $NaHCO_3$ (2 mL) and extracted with $CH_2Cl_2$ (3×5 mL). The combined extracts were washed with saturated aqueous $NaHSO_3$ (5 mL) then dried ($Na_2SO_4$), filtered and concentrated in vacuo. The crude residue was purified on 4 g silica (hexanes→EtOAc, gradient) to afford 3.5 mg (52%) of 26.

Step 10. Saponification of 26 to Give 27.

Aqueous 1 N lithium hydroxide (0.05 mL, 0.05 mmol) was added to a solution of ester 26 (3.5 mg, 0.0077 mmol) in THF (0.1 mL). After 3 d at room temperature, the volatiles were evaporated under a stream of nitrogen. The residue was diluted with water (1.0 mL), acidified with 1 N aqueous HCl (0.5 mL), and extracted with EtOAc (3×2 mL). The combined extracts were washed with brine (5 mL), dried ($Na_2SO_4$), filtered and concentrated in vacuo to afford 2.5 mg (74%) of the title compound (27).

Scheme 7

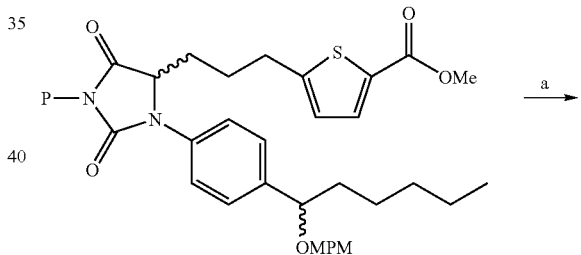

13r

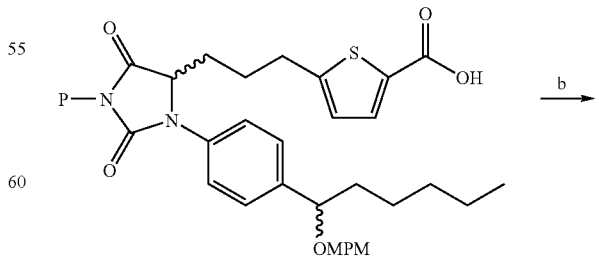

29

49
-continued

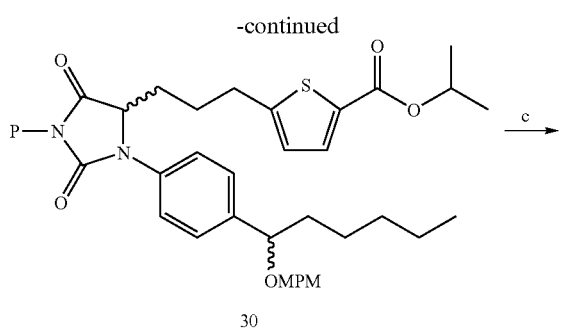
30

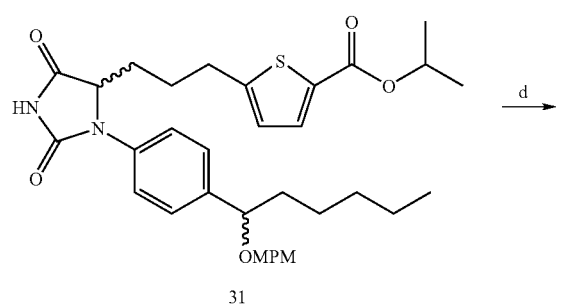
31

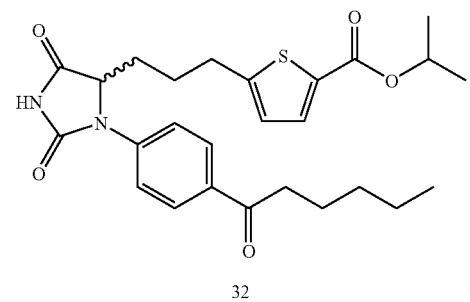
32

(a) LiOH (aq.), THF; (b) i-PrI, DBU, acetone; (c) CAN, H₂O, MeCN;
(d) Dess-Martin periodinane, CH₂Cl₂.

Example 2

5-(3-(3-(4-(1-hydroxyhexyl)phenyl)-2,5-dioxoimidazolidin-4-yl)propyl)thiophene-2-carboxylic acid (14r)

Step 1. Reduction of 26 to Give 28

Sodium borohydride (1 mg, 0.026 mmol) was added in one portion to a solution of 26 (7 mg, 0.015 mmol) in $CH_2Cl_2$ (0.1 mL) and MeOH (0.1 mL). After 30 min, the reaction was quenched with saturated aqueous $NH_4Cl$ and extracted with $CH_2Cl_2$ (3×8 mL). The combined extracts were dried ($Na_2SO_4$), filtered and concentrated in vacuo. The crude residue was purified on 4 g silica (40% EtOAc/hexanes→EtOAc, gradient) to afford 7 mg (quant.) of 28.

Step 2. Saponification of 28 to Give 14r

In accordance with the procedure of Example 1, step 10, ester 28 (7 mg, 0.015 mmol) was converted into 6.5 mg (96%) of the title compound (14r).

50

Example 3

Isopropyl 5-(3-(3-(4-(1-hydroxyhexyl)phenyl)-2,5-dioxoimidazolidin-4-yl)propyl)thiophene-2-carboxylate (31)

Step 1. Saponification of 13r to Give 2

In accordance with the procedure of Example 1, step 10, ester 13r (90 mg, 0.123 mmol) was converted into 86 mg (97%) of 29 after purification on 4 g silica ($CH_2Cl_2$→15% MeOH/$CH_2Cl_2$, gradient).

Step 2. Esterification of 29 to Give 30

1,8-Diazabicyclo[5.4.0]undec-7-ene (DBU, 36 µL, 0.24 mmol) and 2-iodopropane (0.40 mL, 4.0 mmol) were added to a solution of acid 29 (86 mg, 0.12 mmol) in acetone (1.2 mL) at room temperature under nitrogen. After 18 h at room temperature, the volatiles were evaporated under a stream of nitrogen. The residue was diluted with water (5 mL), acidified with 1.0 N HCl (5 mL) extracted with EtOAc (3×30 mL). The combined extracts dried ($Na_2SO_4$), filtered and concentrated in vacuo. Purification of the residue by flash column chromatography on 12 g silica (hexanes→60% EtOAc/hexanes, gradient) afforded 72 mg (79%) of 30.

Step 3. Deprotection of 30 to Give 31

Water (0.2 mL) and CAN (209 mg, 0.38 mmol) were added to a solution of 30 (72 mg, 0.095 mmol) in MeCN (1.9 mL). After 4 h at room temperature, the reaction mixture was quenched with saturated aqueous $NaHCO_3$ (20 mL) and extracted with EtOAc (3×35 mL). The combined extracts were washed with saturated aqueous $NaHSO_3$ (2×30 mL) and brine (30 mL) then dried ($Na_2SO_4$), filtered and concentrated in vacuo. The crude residue was purified on 12 g silica (hexanes→EtOAc, gradient) to afford 16 mg (35%) of the title compound (31).

Example 4

Isopropyl 5-(3-(3-(4-hexanoylphenyl)-2,5-dioxoimidazolidin-4-yl)propyl)thiophene-2-carboxylate (32)

Dess-Martin periodinane (9 mg, 0.021 mmol) was added to a solution of 31 (9 mg, 0.016 mmol) in $CH_2Cl_2$ (0.16 mL) at room temperature. After 4 h the reaction mixture was diluted with 20% EtOAc/hexanes (2 mL) and filtered through celite, washing with additional 20% EtOAc/hexanes (2 mL). The filtrate was concentrated in vacuo. The crude residue was purified on 4 g silica (hexanes→EtOAc, gradient) to afford 4.5 mg (56%) of the title compound (32).

In Vitro Testing

U.S. patent application Ser. No. 11/553,143, filed on Oct. 26, 2006, incorporated by reference herein, describes the methods used to obtain the in vitro data in the table below.

| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flipr EC50 | KI | hFP | hEP1 | hEP3A | hTP | hIP | hDP |
| 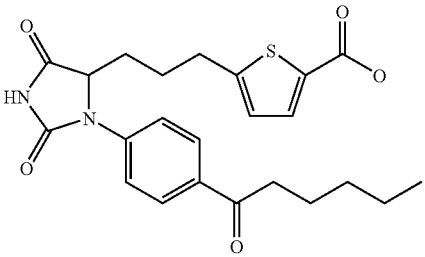 | 17 | 0.2 | 4.5 | 17515 | 3243 | NA | NA | 131 | NA | NA | 8807 |
| 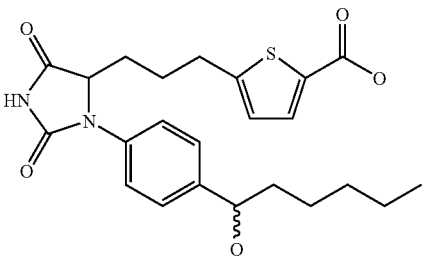 | 3.5 | 0.1 | 5 | NT | >10000 | NA | NA | 10 | NA | NA | 17379 |

In Vivo Testing

U.S. Pat. No. 7,091,231 describes the methods used to carry out the tests reported below.

Isopropyl 5-(3-(3-(4-(1-hydroxyhexyl)phenyl)-2,5-dioxoimidazolidin-4-yl)propyl)thiophene-2-carboxylate (31) was tested in normotensive dogs at 0.003%, dosing once daily for 5 days. The maximum intraocular pressure (IOP) decrease from baseline was 7.7 mmHg (45%) at 102 h; the maximum ocular surface hyperemia (OSH) score was 2.5 at 26 h.

From the methods disclosed herein, a person of ordinary skill in the art can prepare the compounds disclosed herein by using the disclosed methods, by adaptations readily ascertainable by those in the art from the disclosure herein, and/or by the knowledge generally available in the art.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound having a structure

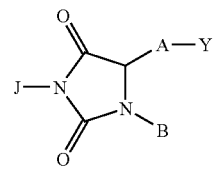

or a pharmaceutically acceptable salt thereof wherein Y is selected from $CO_2R^2$, $CON(R^2)_2$, $CON(OR^2)R^2$, $CON(CH_2CH_2OH)_2$, $CON(CH_2CH_2OH)$, $CH_2OH$, $P(O)(OH)_2$, $CONHSO_2R^2$, $SO_2N(R^2)_2$, $SO2NHR^2$,

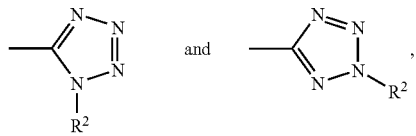

wherein each $R^2$ is independently H, $C_1$-$C_6$ alkyl, unsubstituted phenyl, or unsubstituted biphenyl;

A is —$(CH_2)_m$—Ar—$(CH_2)_o$— wherein Ar is interarylene or heterointerarylene, the sum of m and o is 1, 2, 3, or 4;

J is H, $R^1$, $C(O)R^1$, or $SO_2R^1$; wherein $R^1$ is $C_{1-6}$ alkyl, phenyl, or biphenyl; and B is aryl or heteroaryl.

2. A compound which is a carboxylic acid or a bioisostere thereof, said carboxylic acid having a structure

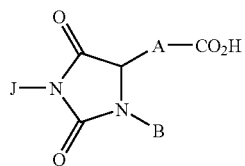

or a pharmaceutically acceptable salt thereof
wherein A-$(CH_2)_m$—Ar—$(CH_2)_o$— wherein Ar is interarylene or heterointerarylene, the sum of m and o is 1, 2, 3, or 4;
J is H, $R^1$, C(O)$R^1$, or $SO_2R^1$; wherein $R^1$ is $C_{1-6}$ alkyl, phenyl, or biphenyl; and
B is aryl or heteroaryl.

3. The compound of claim 2 wherein B is substituted phenyl.

4. The compound of claim 3 having a structure

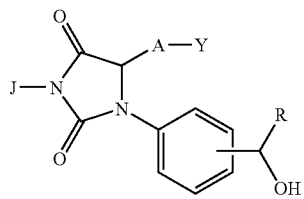

or a pharmaceutically acceptable salt thereof;
wherein R is hydrogen or $C_{1-10}$ hydrocarbyl.

5. The compound of claim 4 wherein R is alkyl.
6. The compound of claim 1 wherein J is H.
7. The compound of claim 5 wherein R is n-pentyl.
8. The compound according to claim 3 wherein A has a structure selected from:

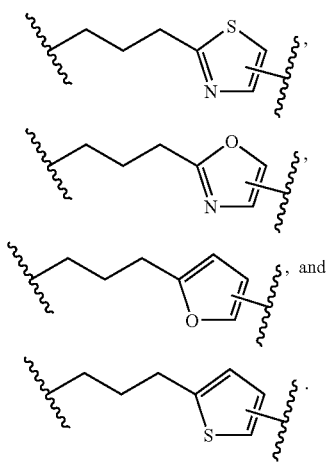

9. The compound according to claim 8 wherein A is 5-(3-propyl)thiophen-2-yl.
10. The compound of claim 3 wherein B is phenyl substituted with $C_{1-10}$ acyl.
11. A pharmaceutical composition comprising a compound of claim 1 in a mammal.

* * * * *